US009725431B2

(12) United States Patent
Zhang et al.

(10) Patent No.: US 9,725,431 B2
(45) Date of Patent: *Aug. 8, 2017

(54) OLIGOMER-TRICYCLIC CONJUGATES

(71) Applicant: NEKTAR THERAPEUTICS, San Francisco, CA (US)

(72) Inventors: Wen Zhang, San Ramon, CA (US); Xuyuan Gu, Foster City, CA (US); Stephanie Allums-Donald, Madison, AL (US); Jennifer Riggs-Sauthier, San Francisco, CA (US)

(73) Assignee: Nektar Therapeutics, San Francisco, CA (US)

( * ) Notice: Subject to any disclaimer, the term of this patent is extended or adjusted under 35 U.S.C. 154(b) by 563 days.

This patent is subject to a terminal disclaimer.

(21) Appl. No.: 14/020,196

(22) Filed: Sep. 6, 2013

(65) Prior Publication Data

US 2014/0100268 A1 Apr. 10, 2014

Related U.S. Application Data

(63) Continuation of application No. 12/744,467, filed as application No. PCT/US2008/013221 on Nov. 28, 2008, now Pat. No. 8,569,380.

(60) Provisional application No. 61/191,635, filed on Sep. 10, 2008, provisional application No. 61/004,483, filed on Nov. 28, 2007.

(51) Int. Cl.
C07D 313/12 (2006.01)
A61K 47/48 (2006.01)
C07C 217/48 (2006.01)

(52) U.S. Cl.
CPC ...... C07D 313/12 (2013.01); A61K 47/48215 (2013.01); C07C 217/48 (2013.01)

(58) Field of Classification Search
None
See application file for complete search history.

(56) References Cited

U.S. PATENT DOCUMENTS

| | | |
|---|---|---|
| 2,554,736 A | 5/1951 | Haefliger et al. |
| 2,948,718 A | 8/1960 | Schindler |
| 3,177,209 A | 4/1965 | Holm |
| 3,205,264 A | 9/1965 | Tristam et al. |
| 3,244,748 A | 4/1966 | Tishler et al. |
| 3,258,399 A | 6/1966 | Tishler et al. |
| 3,271,451 A | 9/1966 | Tishler et al. |
| 3,272,826 A | 9/1966 | Jucker et al. |
| 3,282,942 A | 11/1966 | Rice et al. |
| 3,299,139 A | 1/1967 | Pedersen |
| 3,312,689 A | 4/1967 | Schmutz et al. |
| 3,409,640 A | 11/1968 | Villani |
| 3,419,547 A | 12/1968 | Schmutz et al. |
| 3,420,851 A | 1/1969 | Bloom et al. |
| 3,438,981 A | 4/1969 | Stach |
| 3,442,949 A | 5/1969 | Wendler |
| 3,454,554 A | 7/1969 | Biel et al. |
| 3,467,650 A | 9/1969 | Schindler et al. |
| 3,527,766 A | 9/1970 | Protiva et al. |
| 3,574,852 A | 4/1971 | Dyrsting et al. |
| 3,622,565 A | 11/1971 | Fouche et al. |
| 3,637,660 A | 1/1972 | Eriksoo et al. |
| 3,642,775 A | 2/1972 | Schindler |
| 3,663,696 A | 5/1972 | Howell et al. |
| 3,758,528 A | 9/1973 | Malen et al. |
| 3,963,778 A | 6/1976 | Schutz et al. |
| 4,097,597 A | 6/1978 | Horrom et al. |
| 4,250,094 A | 2/1981 | Hester, Jr. |
| 4,609,664 A | 9/1986 | Hasspacher |
| 5,672,662 A | 9/1997 | Harris et al. |
| 6,214,820 B1 | 4/2001 | Jeppesen et al. |
| 8,569,380 B2 | 10/2013 | Zhang et al. |
| 2005/0136031 A1 | 6/2005 | Bentley et al. |
| 2010/0168232 A1 | 7/2010 | Riggs-Sauthier et al. |
| 2010/0298296 A1 | 11/2010 | Zhang et al. |
| 2012/0046279 A1 | 2/2012 | Gu et al. |

FOREIGN PATENT DOCUMENTS

| | | |
|---|---|---|
| DE | 2030492 A1 | 2/1971 |
| DE | 2030492 B2 | 10/1974 |
| EP | 0 047 226 | 5/1985 |
| GB | 905692 | 9/1962 |
| GB | 961105 | 6/1964 |
| GB | 1069603 | 5/1967 |
| GB | 1191800 | 5/1970 |
| GB | 1269551 | 4/1972 |
| WO | WO 96/16541 | 6/1996 |
| WO | WO 02/098949 | 12/2002 |
| WO | WO 2005/020913 | 3/2005 |
| WO | WO 2005/058367 | 6/2005 |
| WO | WO 2005/084654 | 9/2005 |

(Continued)

OTHER PUBLICATIONS

Zacchigna. Il Farmaco, 2003, 58, 1307-12.*
Blair, et al., "Roles of Tetrodotoxin (TTX)-Sensitive Na+ Current, TTX-Resistant Na+ Current, and Ca2+ Current in the Action Potentials of Nociceptive Sensory Neurons," The J. of Neurosci, vol. 22, No. 23, pp. 10277-1029, (Dec. 1, 2002).
Brodie, Lancet, 345, 476-479, (1995).
Chen, et al., "Synthesis and Properties of ABA Amphiphiles," J. Org. Chem., vol. 64, pp. 6870-6873, (1999).
Crumb, et al., "Comparison of Ito in young and adult human atrial myocytes: evidence for developmental changes," Amer. Physiol. Soc., vol. 268, pp. H1335-H1342, (1995).
Dal Pozzo, et al., "New highly water-soluble phenytoin prodrugs," Intl J. of Pharma., vol. 81, pp. 263-265, (1992).
Dulsat, et al., "Eslicarbazepine Acetate", Drugs of the Future, vol. 34, No. 3, pp. 189-195, (2009).

(Continued)

Primary Examiner — Noble Jarrell

(57) ABSTRACT

The invention provides small molecule drugs that are chemically modified by covalent attachment of a water-soluble oligomer. A conjugate of the invention, when administered by any of a number of administration routes, exhibits characteristics that are different from the characteristics of the small molecule drug not attached to the water-soluble oligomer.

11 Claims, 4 Drawing Sheets

(56) References Cited

FOREIGN PATENT DOCUMENTS

| WO | WO 2006/088786 | 8/2006 | | |
|----|----|----|----|----|
| WO | 2008085297 | * | 7/2008 | ............ A01N 45/00 |
| WO | WO 2008/085927 A2 | 7/2008 | | |
| WO | WO 2009/073154 | 6/2009 | | |
| WO | WO 2009/151590 | 12/2009 | | |
| WO | WO 2010/088340 | 8/2010 | | |

OTHER PUBLICATIONS

Ertl, et al., "Fast Calculation of Molecular Polar Surface Area as a Sum of Fragment-Based Contributions and Its Application to the Prediction of Drug Transport Properties," J. Med. Chem., vol. 43, pp. 3714-3717, (2000).
Haasz, et al., "Synthesis of New, Potentially CNS Active Dibenz[b,f]azepine Derivatives," Arch. Pharm. Pharm. Med. Chem., vol. 329, No. 12, pp. 551-553, (1996).
Hanze, et al., "Dibenzo[b,e][1,4]diazepines," J. of Med. Chem., vol. 6, pp. 767-771, (Nov. 1963).
Hirata, et al., "Potential CNS Antitumor Agents-Phenothiazines II: Fluphenazine Analogs," J. of Pharma. Sci. Amer. Pharma. Assoc., vol. 67, No. 2, pp. 157-162, (Jan. 1, 1978).
Hunziker, et al., "Dibenzo-azepine, -diazepine, -oxazepine und -thiazepine," Helvetica Chimica Acta., vol. 47, No. 5, pp. 1163-1172, (1964).
Kelder, et al., "Polar Molecular Surface as a Dominating Determinant for Oral Absorption and Brain Penetration of Drugs," Pharmaceu. Res., vol. 16, No. 10, pp. 1514-1519, (1999).
Kolesnikov, et al., "Topical Opioids in Mice: Analgesia and Reversal of Tolerance by a Topical N-Methyl-D-Aspartate Antagonist," The J. of Pharmaco. and Exp. Therap., vol. 290, No. 1, pp. 247-252, (1999).
Lu, et al., "Podand-Catalyzed Nucleophilic Aromatic Substitutions of Anthraquinones: A Novel Synthetic Approach and a Mechanistic Suggestion from Solid-State Data," The J. of Org. Chem., vol. 55, No. 8, pp. 2269-2270, (Apr. 13, 1990).
Max, The New England Journal of Medicine, 326(19), 1250-1256, (1992).
McCleane, Journal of Clinical Pharmacology, 49, 574-579, (2000).
Stach, et al., "Beitrage zur Entwicklung psychotroper Stoffe, 2. Mitt.," Monatshefte Fur Chemie, vol. 93, No. 4, pp. 896-904, (May 9, 1962).
PCT International Search Report corresponding to PCT Application No. PCT/US2008/013221 dated May 18, 2009.
PCT International Preliminary Report on Patentability corresponding to PCT Application No. PCT/US2008/013221 dated Jun. 10, 2010.
PCT International Search Report corresponding to PCT Application No. PCT/US2011/021733 dated Jul. 11, 2011.
PCT International Preliminary Report on Patentability corresponding to PCT Application No. PCT/US2011/021733 dated Aug. 2, 2012.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-1$^{st}$, (Jan. 2003).
NOF Corporation, PEG Derivatives, Phospholipid and Drug Delivery Materials for Pharmaceuticals, 27 pages, Catalogue 2003-2$^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Chinese Notification of the First Office Action corresponding to Chinese Patent Application No. 200880118154.3 dated Jun. 21, 2011.
Chinese Notification of the Second Office Action corresponding to Chinese Patent Application No. 200880118154.3 dated May 11, 2012.
Chinese Notification of the Third Office Action corresponding to Chinese Patent Application No. 200880118154.3 dated Oct. 24, 2012.
European Communication corresponding to European Patent Application No. 08 857 684.8 dated Jul. 7, 2010.
European Communication corresponding to European Patent Application No. 08 857 684.8 dated Dec. 15, 2010.
European Communication corresponding to European Patent Application No. 08 857 684.8 dated Aug. 24, 2011.
Israel First Substantive Examination Report corresponding to Israel Patent Application No. 205966 dated Jan. 24, 2013.G.
Australian Patent Examination Report No. 1 corresponding to Australian Patent Application No. 2008331868 date of issue Jun. 21, 2013.
European Communication corresponding to European Patent Application No. 08 857 684.8 dated Jun. 18, 2013.
Canadian Communication in Canadian Patent Application No. 2,704,836 dated Sep. 11, 2014.
English Translation of Japanese Notice of Reasons for Rejection in Japanese Patent Application No. 2010-536016 dated Jan. 22, 2014.
English Translation of Korean Notice of Grounds for Rejection in Korean Patent Application No. 2010-7011331 dated Jan. 13, 2015.
Japanese Notice of Reasons for Rejection corresponding to Japanese Patent Application No. 2010-536016 dated Sep. 25, 2013.
Mexican Official Letter corresponding to Mexican Patent Application No. MX/a/2010/005813 dated Oct. 16, 2013.
McCleane, "Topical application of doxepin hydrochloride, capsaicin and a combination of both produces analgesia in chronic human neuropathic pain: a randomized, double-blind, place-controlled study," Br. J. Clin. Pharmacol., vol. 49, pp. 574-579, (2000).
First Examination Report in Indian Patent Application No. 3310/DELNP/2010 dated Mar. 31, 2015.

* cited by examiner

[Ligand]: 1.0e-6
Kd: 9.0e-10

OLIGOMER-TRICYCLIC CONJUGATES

CROSS REFERENCE TO RELATED APPLICATIONS

This application is a divisional application of U.S. patent application Ser. No. 12/744,467, filed 29 Jul. 2010, now U.S. Pat. No. 8,569,380, which claims the benefit of priority under 35 U.S.C. §119(e) to U.S. Provisional Patent Application Ser. No. 61/004,483, filed 28 Nov. 2007, and U.S. Provisional Application Ser. No. 61/191,635, filed 10 Sep. 2008, and both of which are hereby incorporated by reference in their entireties.

FIELD OF THE INVENTION

This invention comprises (among other things) chemically modified tricyclics that possess certain advantages over tricyclics lacking the chemical modification. The chemically modified tricyclics described herein relate to and/or have application(s) in (among others) the fields of drug discovery, pharmacotherapy, physiology, organic chemistry and polymer chemistry.

BACKGROUND OF THE INVENTION

Clinical depression (also called major-depressive disorder or unipolar depression) is a common psychiatric disorder, characterized by a persistent lowering of mood, loss of interest in usual activities and diminished ability to experience pleasure.

While the term "depression" is commonly used to describe a temporary decreased mood when one "feels blue," clinical depression is a serious illness that involves the body, mood, and thoughts and cannot simply be willed or wished away. It is often a disabling disease that affects a person's work, family and school life, sleeping and eating habits, general health and ability to enjoy life. The course of clinical depression varies widely: depression can be a once in a life-time event or have multiple recurrences, it can appear either gradually or suddenly, and either last for few months or be a life-long disorder. Having depression is a major risk factor for suicide; in addition, people with depression suffer from higher mortality from other causes. Clinical depression is usually treated by psychotherapy, antidepressants, or a combination of the two.

Neuropathy is a disease of the peripheral nerve or nerves. The four major forms of nerve damage are polyneuropathy, autonomic neuropathy, mononeuropathy, and mononeuritis multiplex. A more common form is peripheral polyneuropathy, which mainly affects the feet and legs. There are other less common forms of neuropathy, for example enteric neuropathy.

Aside from diabetes (i.e., diabetic neuropathy), the common causes of neuropathy are herpes zoster infection, HIV-AIDS, toxins, alcoholism, chronic trauma (such as repetitive motion disorders) or acute trauma (including surgery), neurotoxicity and autoimmune conditions such as celiac disease. Neuropathic pain is common in cancer as a direct result of the cancer on peripheral nerves (e.g., compression by a tumor), as a side effect of many chemotherapy drugs, and as a result of electrical injury. In many cases the neuropathy is "idiopathic," meaning no cause is found.

Neuropathic pain is usually perceived as a steady burning and/or "pins and needles" and/or "electric shock" sensations and/or tickling. The difference is due to the fact that "ordinary" pain stimulates only pain nerves, while a neuropathy often results in the firing of both pain and non-pain (touch, warm, cool) sensory nerves in the same area, producing signals that the spinal cord and brain do not normally expect to receive.

Neuropathic pain may be difficult to treat. A systematic review of randomized controlled trials found that the best treatments are tricyclics, anticonvulsants, and capsaicin. Tricyclic antidepressants are used in numerous applications; mainly indicated for the treatment of clinical depression, neuropathic pain, nocturnal enuresis, and ADHD, but they have also been used successfully for headache (including migraine headache), anxiety, insomnia, smoking cessation, bulimia nervosa, irritable bowel syndrome, narcolepsy, pathological crying or laughing, persistent hiccups, interstitial cystitis, and ciguatera poisoning, and as an adjunct in schizophrenia.

It is generally thought that tricyclic antidepressants work by inhibiting the re-uptake of the neurotransmitters norepinephrine, dopamine, or serotonin by nerve cells. Tricyclics may also possess affinity for muscarinic and histamine H1 through H4 receptors to varying degrees. Although norepinephrine and dopamine are generally considered stimulatory neurotransmitters, tricyclic antidepressants also increase the effects on H1 histamine, and thus most have sedative effects and may also be useful as anti-histaminic compounds.

The utility of antidepressants and anticonvulsants has been limited by potential adverse effects on the central nervous system such as bad dreams, drowsiness, blurred vision, decreased gastro-intestinal mobility and secretion, difficulty with urination, hyperthermia, and dry mouth. As a consequence, pharmacotherapy with tricyclics would be improved if these and/or other side effects associated with their use could be decreased. Thus, there is a large unmet need for developing novel tricyclic compounds.

The present invention seeks to address these and other needs in the art.

SUMMARY OF THE INVENTION

In one or more embodiments of the invention, a compound is provided, the compound comprising a tricyclic residue covalently attached via a stable or degradable linkage to a water-soluble, non-peptidic oligomer.

Exemplary compounds of the invention include those having the following structure:

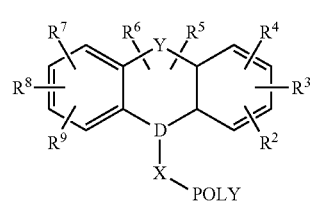

Formula I-C wherein:
D is C or N;
Y is selected from the group consisting of —CH$_2$—, —CH—, —CH$_2$CH$_2$—, —CH=CH—, —CH$_2$—S—, CH$_2$—O—, CH$_2$—NH—, —S—CH$_2$—, —O—CH$_2$, —NH—CH$_2$, —HN—, —O—, —N=C—, —C=N—, and —S—, unsubstituted or optionally substituted;
X is a spacer moiety; and
POLY is a water-soluble, non-peptidic oligomer.

The "tricyclic residue" is a compound having a structure of a tricyclic compound that is altered by the presence of one or more bonds, which bonds serve to attach (either directly or indirectly) one or more water-soluble, non-peptidic oligomers. Exemplary tricyclics have a structure encompassed by at least one of the structures defined herein as Formula I:

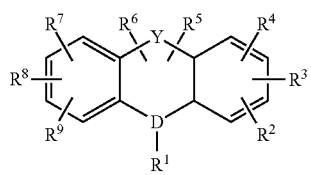

Formula I wherein:
D and $R^1$, taken together, are selected from the group consisting of —HC—$R^1$, —C=$R^1$, and —HN—$R^1$;
$R^1$ is selected from the group consisting of alkyl, amino, acylamino, acyl, amido, aryloxy, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, and 4-(methoxy-lower alkyl)-1-piperizinyl, unsubstituted or optionally substituted;
Y is selected from the group consisting of —$CH_2$—, —CH—, —$CH_2CH_2$—, —CH=CH—, —$CH_2$—S—, $CH_2$—O—, $CH_2$—NH—, —S—$CH_2$—, —O—$CH_2$, —NH—$CH_2$, —HN—, —O—, —N=C—, —C=N—, and —S—, unsubstituted or optionally substituted; and
one or more of $R^2$, $R^3$, $R^4$, $R^5$, $R^6$, $R^7$, $R^8$, $R^9$, each are independently selected from the group consisting of nil, hydrogen, halo, cyano, hydroxy, carboxy, keto, thioketo, amino, acylamino, acyl, amido, aryloxy, alkyl, alkenyl, alkynyl, heteroalkyl, haloalkyl, alkoxy, dioxo, aryl, heteroaryl, cycloalkyl, and heterocycloalkyl, unsubstituted or optionally substituted.

In one or more embodiments of the invention, a composition is provided, the composition comprising a compound comprising a tricyclic residue covalently attached via a stable or degradable linkage to a water-soluble and non-peptidic oligomer, and optionally, a pharmaceutically acceptable excipient.

In one or more embodiments of the invention, a dosage form is provided, the dosage form comprising a compound comprising a tricyclic residue covalently attached via a stable or degradable linkage to a water-soluble, non-peptidic oligomer, wherein the compound is present in a dosage form.

In one or more embodiments of the invention, a method is provided, the method comprising covalently attaching a water-soluble, non-peptidic oligomer to a tricyclic.

In one or more embodiments of the invention, a method is provided, the method comprising administering a compound comprising a tricyclic residue covalently attached via a stable or degradable linkage to a water-soluble, non-peptidic oligomer.

These and other objects, aspects, embodiments and features of the invention will become more fully apparent to one of ordinary skill in the art when read in conjunction with the following detailed description.

DETAILED DESCRIPTION OF THE INVENTION

Figure 1:
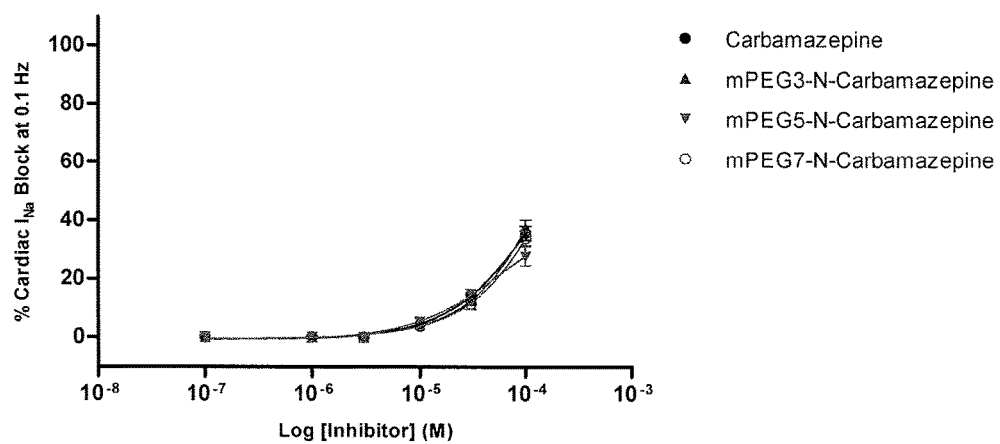
FIG. 1 shows blocking effects of carbamazepine and its conjugates on sodium current at 0.1 Hz (A) vs. 3 Hz (B) in isolated human atrial myocytes. Data are mean±SEM.
Figure 1:
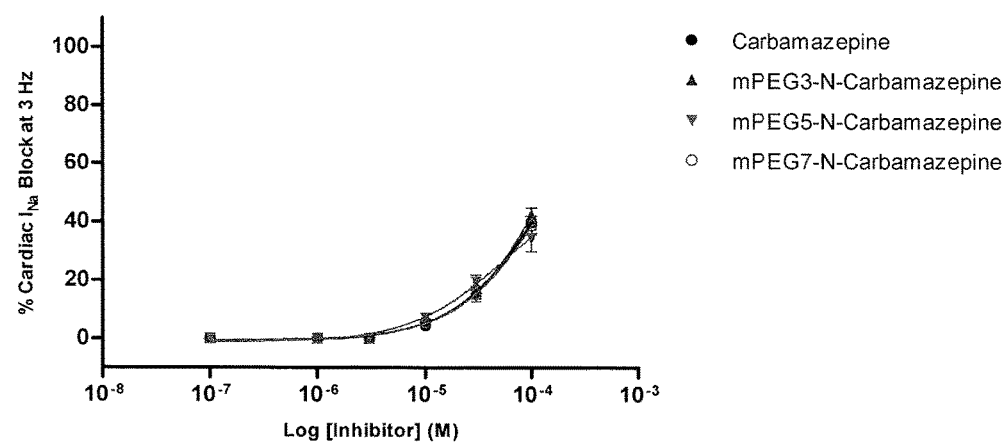

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with present the invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" an oligoethylene glycol is one in which substantially all (preferably all) monomeric subunits are ethylene oxide subunits, though the oligomer may contain distinct end capping moieties or functional groups, e.g., for conjugation. PEG oligomers for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG oligomers, the variable "n" ranges from about 1 to 30, preferably from about 2 to about 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" and "terminally capped" are interchangeably used herein to refer to a terminal or endpoint of a polymer having an end-capping moiety. Typically, although not necessarily, the end-capping moiety comprises a hydroxy or $C_{1-20}$ alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in $CH_3O(CH_2CH_2O)_n$— and $CH_3(OCH_2CH_2)_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

The term "targeting moiety" is used herein to refer to a molecular structure that helps the conjugates of the invention to localize to a targeting area, e.g., help enter, permeate, or penetrate a cell, or bind a receptor. Preferably, the targeting moiety comprises of vitamin, cofactor, antibody, antigen, receptor, DNA, RNA, sialyl Lewis X antigen, hyaluronic acid, sugars, cell specific lectins, steroid or steroid derivative, RGD peptide, cell penetrating or cell targeting moiety, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Branched", in reference to the geometry or overall structure of an oligomer, refers to an oligomer having two or more polymer "arms" from a branch point.

"Forked", in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, thiolesters, and carbonates.

An "enzymatically degradable linkage" means a linkage that is subject to degradation by one or more enzymes.

A "stable" linkage or bond refers to a bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000, if the oligomer were not attached to the moiety derived from a small molecule drug. A composition comprised of monodisperse conjugates may however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the moiety derived from a small molecule drug. A composition comprised of bimodal conjugates can include, however, one or more nonconjugate substances such as solvents, reagents, excipients, and so forth.

A "tricyclic" refers to an organic, inorganic, or organometallic compound typically having a molecular weight of less than about 1000 Daltons and having some degree of activity as tricyclic therapeutic as described herein.

A "biological membrane" is any membrane made of cells or tissues that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate," provides a measure of a compound's ability to cross a biological membrane (such as the blood-brain barrier (BBB)). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are described herein and/or in the relevant literature, and/or may be determined by one of ordinary skill in the art.

A "reduced rate of metabolism" in reference to the present invention, refers to a measurable reduction in the rate of metabolism of a water-soluble oligomer-small molecule drug conjugate as compared to the rate of metabolism of the small molecule drug not attached to the water-soluble oligomer (i.e., the small molecule drug itself) or a reference standard material. In the special case of "reduced first pass rate of metabolism," the same "reduced rate, of metabolism" is required except that the small molecule drug (or reference standard material) and the corresponding conjugate are administered orally. Orally administered drugs are absorbed from the gastro-intestinal tract into the portal circulation and may pass through the liver prior to reaching the systemic circulation. Because the liver is the primary site of drug metabolism or biotransformation, a substantial amount of drug may be metabolized before it reaches the systemic circulation. The degree of first pass metabolism, and thus, any reduction thereof, may be measured by a number of different approaches. For instance, animal blood samples may be collected at timed intervals and the plasma or serum analyzed by liquid chromatography/mass spectrometry for metabolite levels. Other techniques for measuring a "reduced rate of metabolism" associated with the first pass metabolism and other metabolic processes are known, described herein and/or in the relevant literature, and/or may be determined by one of ordinary skill in the art. Preferably, a conjugate of the invention may provide a reduced rate of metabolism reduction satisfying at least one of the following values: at least about 30%; at least about 40%; at least about 50%; at least about 60%; at least about 70%; at least about 80%; and at least about 90%. A compound (such as a small molecule drug or conjugate thereof) that is "orally bioavailable" is one that preferably possesses a bioavailability when administered orally of greater than 25%, and preferably greater than 70%, where a compound's bioavailability is the fraction of administered drug that reaches the systemic circulation in unmetabolized form.

"Alkyl" refers to a hydrocarbon chain ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, butyl, t-butyl.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

"Pharmaceutically acceptable excipient" or "pharmaceutically acceptable carrier" refers to component that may be included in the compositions of the invention causes no significant adverse toxicological effects to a patient.

The term "aryl" means an aromatic group having up to 14 carbon atoms. Aryl groups include phenyl, naphthyl, biphenyl, phenanthrenyl, naphthalenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, cyano, nitro, alkyl (e.g., $C_{1-6}$ alkyl), alkoxy (e.g., $C_{1-6}$ alkoxy), benzyloxy, carboxy, aryl, and so forth.

Chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g., $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding multivalent moiety, arylene). All atoms are understood to have their normal number of valences for bond formation (i.e., 1 for H, 4 for carbon, 3 for N, 2 for O, and 2, 4, or 6 for S, depending on the oxidation state of the S).

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount may depend upon numerous factors, e.g., the particular active agent, the components and physical characteristics of the composition, intended patient population, patient considerations and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterodifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, and includes both humans and animals.

"Optional" or "optionally" means that the subsequently described circumstance may but need not necessarily occur, so that the description includes instances where the circumstance occurs and instances where it does not.

"Nil" refers to the absence of a substituent group. Thus, when a substituent is nil, the substituent may be represented in the structure as a chemical bond or hydrogen in the resulting structure.

As indicated above, the present invention is directed to (among other things) a compound comprising a tricyclic residue covalently attached via a stable or degradable linkage to a water-soluble, non-peptidic oligomer.

In one or more embodiments of the invention, a compound is provided, the compound comprising a tricyclic residue covalently attached via a stable or degradable linkage to a water-soluble, non-peptidic oligomer, wherein the tricyclic compound has a structure encompassed by the following formula:

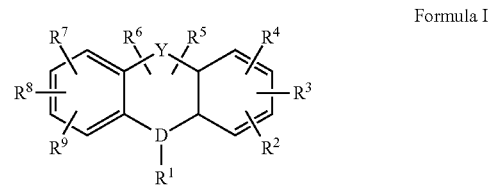

Formula I wherein:
  D and $R^1$, taken together, are selected from the group consisting of —HC—$R^1$, —C=$R^1$, and
  $R^1$ is selected from the group consisting of alkyl, amino, acylamino, acyl, amido, aryloxy, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, and 4-(methoxy-lower alkyl)-1-piperizinyl, unsubstituted or optionally substituted;
  Y is selected from the group consisting of —$CH_2$—, —CH—, —$CH_2CH_2$—, —CH=CH—, —$CH_2$—S—, $CH_2$—O—, $CH_2$—NH—, —S—$CH_2$—, —O—$CH_2$, —NH—$CH_2$, —HN—, —O—, —N=C—, —C=N—, and —S—, unsubstituted or optionally substituted; and
  one or more of $R^2$, $R^3$, $R^4$, $R^5$, $R^6$, $R^7$, $R^8$, $R^9$, each are independently selected from the group consisting of nil, hydrogen, halo, cyano, hydroxy, carboxy, keto, thioketo, amino, acylamino, acyl, amido, aryloxy, alkyl, alkenyl, alkynyl, heteroalkyl, haloalkyl, alkoxy, dioxo, aryl, heteroaryl, cycloalkyl, and heterocycloalkyl, unsubstituted or optionally substituted.

Examples of specific tricyclic compounds include those selected from the group consisting of amineptine, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, lofepramine, melitracen, metapramine, nortriptyline, opipramol, propizepine, protriptyline, quinupramine, tianeptine, trimipramine, and carbamazepine.

It is believed that an advantage of the compounds of the present invention is their ability to retain some degree of tricyclic activity while also exhibiting a decrease in metabolism. Although not wishing to be bound by theory, it is believed that the tricyclic residue- and oligomer-containing compounds described herein—in contrast to the oligomer-free "original" tricyclic structure—are not metabolized as readily because the oligomer serves to reduce the overall affinity of the compound to substrates that may metabolize tricyclics. In addition (and again, not wishing to be bound by theory), the extra size introduced by the oligomer—in contrast to the oligomer-free "original" tricyclic structure—reduces the ability of the compound to cross the blood-brain barrier. Even should the linkage between the residue of the tricyclic and the oligomer be degradable, the compound still offers advantages (such as avoiding first-pass metabolism upon initial absorption).

Use of discrete oligomers (e.g., from a monodisperse or bimodal composition of oligomers, in contrast to relatively impure compositions) to form oligomer-containing compounds may advantageously alter certain properties associated with the corresponding small molecule drug. For instance, a compound of the invention, when administered by any of a number of suitable administration routes, such as parenteral, oral, transdermal, buccal, pulmonary, or nasal, exhibits reduced penetration across the blood-brain barrier. It is preferred that the compounds of the invention exhibit slowed, minimal or effectively no crossing of the blood-brain barrier, while still crossing the gastro-intestinal (GI) walls and into the systemic circulation if oral delivery is intended. Moreover, the compounds of the invention maintain a degree of bioactivity as well as bioavailability in comparison to the bioactivity and bioavailability of the compound free of all oligomers.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

For compounds whose degree of blood-brain barrier crossing ability is not readily known, such ability may be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses may be conducted, for example, by contract research organizations such as Absorption Systems, Exton, Pa.). In one example of the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., *J. Med. Chem.* 2000, 43, 3714-3717; and Kelder, J., et al., *Pharm. Res.* 1999, 16, 1514-1519.

With respect to the blood-brain barrier, the water-soluble, non-peptidic oligomer-small molecule drug conjugate exhibits a blood-brain barrier crossing rate that is reduced as compared to the crossing rate of the small molecule drug not attached to the water-soluble, non-peptidic oligomer. Exemplary reductions in blood-brain barrier crossing rates for the compounds described herein include reductions of: at least about 5%; at least about 10%; at least about 25%; at least about 30%; at least about 40%; at least about 50%; at least about 60%; at least about 70%; at least about 80%; or at least about 90%, when compared to the blood-brain barrier crossing rate of the small molecule drug not attached to the water-soluble oligomer. A preferred reduction in the blood-brain barrier crossing rate for a conjugate of the invention is at least about 20%.

As indicated above, the compounds of the invention include a tricyclic residue. Assays for determining whether a given compound (regardless of whether the compound includes a water-soluble, non-peptidic oligomer or not) can act as an antidepressant, anticonvulsant, or as an analgesic are described infra.

The variables, notations, and symbols used in the following paragraphs with respect to formula may not relate to other paragraphs. Therefore, definitions of the notations and symbols in each paragraph are normally limited to it and should not be used to construe other paragraphs, unless indicated otherwise.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

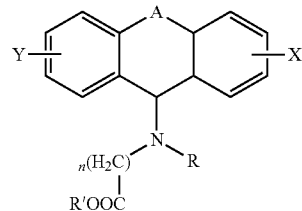

wherein:
A is a bridge selected from the following radicals —(CH$_2$)$_m$—, and —CH=CH—, in which:
m is an integer of from 1 to 3 inclusive;
X and Y are selected from the group consisting of hydrogen and halo selected from fluoro, chloro and bromo;
R and R' are selected from the group consisting of hydrogen and lower alkyl having from one to five carbon atoms inclusive; and
n is an integer of from 1 to 12 inclusive.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula: (3'-dimethylaminopropylidene)-dibenzo(a,d)-cyclohepta-1,4-diene N-oxide, and or the hydrochloric acid addition salt thereof.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula: a formula selected from the group consisting of 2-chloro-11-(1-piperizinyl)dibenz(b,f)[1,4]ox-azepine, 2-chloro-1'-(1-piperizinyl)dibenz(b,f)[1,4]ox-azepine hydrochloride, 2-chloro-11-(1-piperizinyl)dibenz(b,f)[1,4]ox-azepine fumarate, 2-chloro-11-(1-piperizinyl)dibenz(b,f)[1,4]ox-azepine sulfate, and 2-chloro-11-(1-piperizinyl)dibenz(b,f)[1,4]ox-azepine diheptanoate.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula: 5-(3'-dimethylamino-2'-methylpropyl)dibenzo[a,d][1,4]-cycloheptadiene.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula: a formula selected from the group consisting of 3-chloro-5-(γ-dimethylamino-propyl)-iminodibenzyl, a pharmaceutically acceptable acid addition salt of 3-chloro-5-(γ-dimethylamino-propyl)-iminodibenzyl, and 3-chloro-5-(γ-dimethylamino-propyl)-iminodibenzyl hydrochloride.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula: a formula selected from the group consisting of

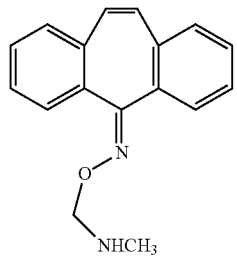

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula: a formula selected from the group consisting of 5-(γ-methylamino-propyl)-iminodibenzyl and nontoxic addition salts thereof, N-(3-methylaminopropyl)-iminodibenzyl, and N-(3-methylaminopropyl)-iminodibenzyl hydrochloride.

In one or more embodiments of the invention, a compound is provided, the compound comprising a tricyclic residue covalently attached via a stable or degradable linkage to a water-soluble, non-peptidic oligomer, wherein the tricyclic is a compound selected from the group consisting of a 10-(basic substituted)-10,11-dihydro-5H-dibenzo[b,e][1,4]diazepine of the formula:

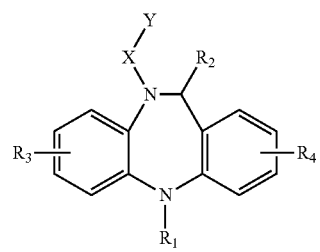

wherein X represents alkylene having between 2 and 3 inclusive carbon atoms; Y is a member of the class consisting of dialkylamino having between 2 and 4 inclusive carbon atoms, pyrrolidino, piperidino, and morpholino; $R_1$ and $R_2$ represent, interchangeably, a member of the class consisting of hydrogen, methyl, and ethyl; and $R_3$ and $R_4$ represent, interchangeably, a member of the class consisting of hydrogen, chloro, methyl, ethyl, methoxy, and ethoxy.

In one or more embodiments of the invention, a compound is provided, the compound comprising a tricyclic residue covalently attached via a stable or degradable linkage to a water-soluble, non-peptidic oligomer, wherein the tricyclic residue is selected from the group consisting of a compound of the formula:

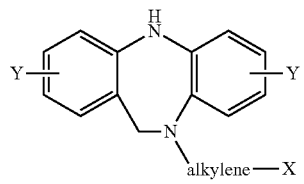

wherein alkylene has 2 to 4 carbons inclusive, and at least two carbons separate X from the heterocyclic nucleus; X is selected from the group consisting of dialkylamino of 2 to 4 carbons, pyrrolidino, piperidino, and morpholino; and each Y is independently selected from the group consisting of hydrogen, chloro, methyl, methoxy, and ethoxy.

In one or more embodiments of the invention, a compound is provided, the compound comprising a tricyclic residue covalently attached via a stable or degradable linkage to a water-soluble, non-peptidic oligomer, wherein the tricyclic is a compound selected from the group consisting of: the substituted 5H-dibenzo[b,e][1,4]diazepine derivatives of the formula:

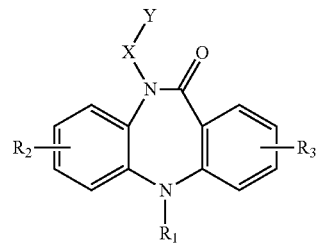

wherein $R_1$ is selected from the class consisting of hydrogen, methyl, and ethyl; —X—Y is a basic radical wherein X is a hydrocarbon chain containing between 2 and 3 inclusive carbon atoms, and Y is selected from the class consisting of dialkylamino having between 2 and 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, and 4-(methoxy-lower alkyl)-1-piperizinyl and $R_2$ and $R_3$ are selected from the class consisting of hydrogen, chloro, methyl, ethyl, methoxy, ethoxy, trifluoromethyl, methylmercapto, and ethylmercapto.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

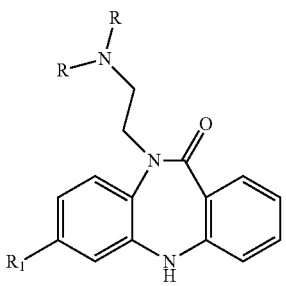

wherein R is a member selected from the group consisting of $CH_3$ and $C_2H_5$, and $R_1$ is a member selected from the group consisting of Cl, $CH_3$, $CF_3$, and $C_2H_5$.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

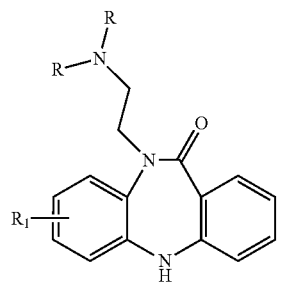

wherein R is a member selected from the group consisting of $CH_3$ and $C_2H_5$, and $R_1$ is a member selected from the group consisting of H, Cl, $CH_3$, $CF_3$, and $C_2H_5$.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula: 11-(3-dimethylaminopropylidene)-6,11-dihydro-dibenz-(b,e)thiepin.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

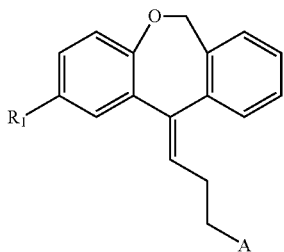

wherein $R_1$ is a member of the group consisting of hydrogen and halo and A is 4-(β-hydroxyethyl-piperidino).

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

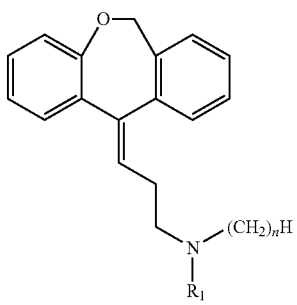

wherein n is a whole number from 0 to 1 and $R_1$ is alkyl having from 1 to 4 carbon atoms.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

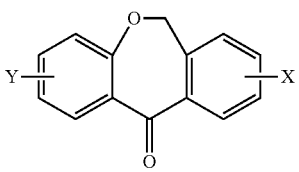

wherein X and Y are each selected from the group consisting of hydrogen, alkyl having from 1 to 4 carbon atoms, alkoxy having from 1 to 4 carbon atoms, thioalkoxy having from 1 to 4 carbon atoms, chloro, fluoro, trifluoromethyl, acyl having from 1 to 4 carbon atoms, and dialkylsulfonamido having from 1 to 8 carbon atoms.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

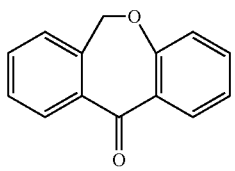

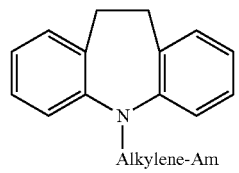

Alkylene-Am

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

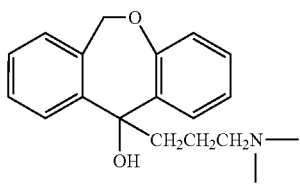

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

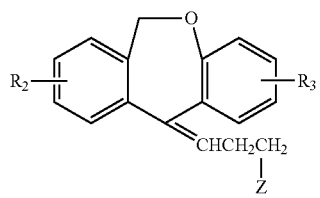

wherein $R_2$ and $R_3$ are each a member of the group consisting of hydrogen, fluoro, chloro, lower alkyl, lower aloxy, lower alkylthio, and trifluoromethyl and Z is di-lower-alkylamino.

In one or more embodiments of the invention, a compound is provided, the compound comprising a tricyclic residue covalently attached via a stable or degradable linkage to a water-soluble, non-peptidic oligomer, wherein the tricyclic compound is selected from the group consisting of a free base and its water soluble acid addition salts, said free base having the formula:

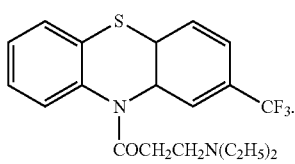

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

wherein alkylene represents an alkylene chain of 2-3 carbon atoms and Am represents a member selected from the group consisting of a low molecular dialkylamino radical, the N-piperidino-, N-morpholino-, and N-pyrrolidino radicals.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

wherein Y is selected from the group consisting of $CH_2$—$CH_2$ and $CH=CH$;

$R^1$ is selected from the group consisting of H and $CH_3$;

$R^2$ represents an alkyl group having a maximum of 4 carbon atoms;

n is selected from the group consisting of 1, 2, and 3;

$R^3$ is selected from the group consisting of phenyl and phenyl substituted with a maximum of three substituents selected from the group consisting of F, Cl, OH, $CF_3$, as well as alkyl and alkoxy containing a maximum of 4 carbon atoms; and a phenyl group having at the 3,4-positions a substituent selected from the group consisting of alkylidenedioxy (having a maximum of 6 carbon atoms), cycloalkylidenedioxy (having a maximum of 6 carbon atoms), and ethylenedioxy;

$R^4$ is selected from the group consisting of H, F, Cl, $OCH_3$, $CF_3$, and $SO_2N(CH_3)_2$.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

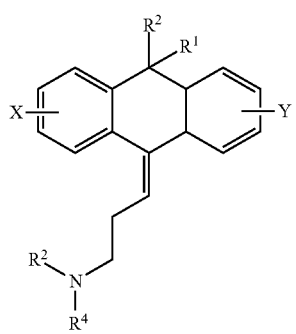

wherein each of R¹ and R² is a lower-alkyl group; X is selected from the group consisting of hydrogen, halo, lower-alkyl and lower-alkyloxy; Y is selected from the group consisting of hydrogen and halo; and

is selected from the group consisting of di-lower-alkylamino, benzyl-lower-alkylamino, and heterocyclic amine radicals, said heterocyclic amines being selected from the group consisting of pyrrolidine, piperidine, morpholine, thiamorpholine, N¹-lower-alkylpiperizine, and C-lower alkyl derivatives of the foregoing.

In one or more embodiments of the invention, a compound is provided, the compound comprising a tricyclic residue covalently attached via a stable or degradable linkage to a water-soluble, non-peptidic oligomer, wherein the tricyclic has a structure encompassed by the following formula:

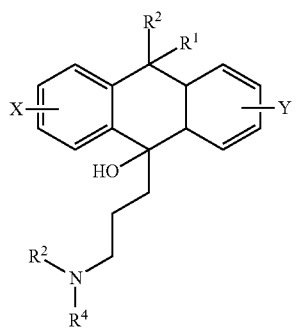

wherein each of R¹ and R² is a lower-alkyl group; X is selected from the group consisting of hydrogen, halo, lower-alkyl and lower-alkyloxy; Y is selected from the group consisting of hydrogen and halo; and

is selected from the group consisting of di-lower-alkylamino, benzyl-lower-alkylamino, the radical of a heterocyclic amine, having a saturated five-membered ring, and the radical of a heterocyclic amine having a saturated six-membered ring, said heterocyclic amines being selected from the group consisting of pyrrolidine, piperidine, morpholine, thiamorpholine, N¹-loweralkylpiperizine, and C-lower alkyl derivatives of the foregoing.

In one or more embodiments of the invention, a compound is provided, the compound comprising a tricyclic residue covalently attached via a stable or degradable linkage to a water-soluble, non-peptidic oligomer, wherein the tricyclic compound has the formula:

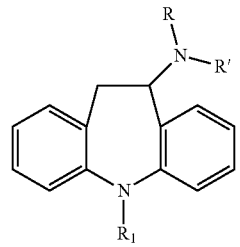

in which R and R' are the same or different and each represent hydrogen or alkyl of one to five carbon atoms, and $R_1$ is hydrogen, alkyl, of one to five carbon atoms, or benzyl.

In one or more embodiments of the invention, a compound is provided, the compound comprising a tricyclic residue covalently attached via a stable or degradable linkage to a water-soluble, non-peptidic oligomer, wherein the tricyclic compound has the formula:

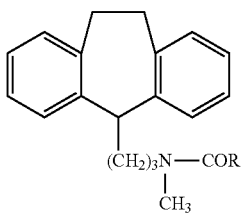

wherein R is selected from the group consisting of hydrogen, lower alkyl, phenyl, and benzyl.

In one or more embodiments of the invention, a compound is provided, the compound comprising a tricyclic residue covalently attached via a stable or degradable linkage to a water-soluble, non-peptidic oligomer, wherein the tricyclic compound has the formula:

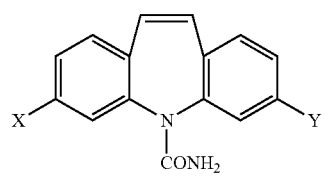

wherein each of X and Y represents a member selected from the group consisting of hydrogen and halo.

In some instances, tricyclics can be obtained from commercial sources. In addition, tricyclics can be obtained through chemical synthesis. Examples of tricyclics as well as synthetic approaches for preparing tricyclics are described in the literature and in, for example, DE2030492A1, DE2030492A, DE2030492132, DE2030492C3, GB1191800A, U.S. Pat. No. 2,554,736, U.S. Pat. No. 2,948,718, U.S. Pat. No. 3,177,209, U.S. Pat. No. 3,205,264, U.S. Pat. No. 3,244,748, U.S. Pat. No. 3,271,451, U.S. Pat. No. 3,299,139, U.S. Pat. No. 3,312,689, U.S. Pat. No. 3,409,640, U.S. Pat. No. 3,419,547, U.S. Pat. No. 3,438,981, U.S. Pat. No. 3,442,949, U.S. Pat. No. 3,454,554, U.S. Pat. No. 3,467,650, U.S. Pat. No. 3,527,766, U.S. Pat. No. 3,574,852, U.S. Pat. No. 3,622,565, U.S. Pat. No. 3,637,660, U.S. Pat. No. 3,663,696, U.S. Pat. No. 3,758,528, U.S. Pat. No. 3,963,778. Each of these (and other) tricyclics can be covalently attached (either directly or through one or more atoms) to a water-soluble and non-peptidic oligomer.

Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300.

The small molecule drug used in the invention, if chiral, may be in a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety. The tricyclic for coupling to a water-soluble, non-peptidic oligomer possesses a free hydroxyl, carboxyl, thio, amino group, or the like (i.e., "handle") suitable for covalent attachment to the oligomer. In addition, the tricyclic may be modified by introduction of a reactive group, preferably by conversion of one of its existing functional groups to a functional group suitable for formation of a stable covalent linkage between the oligomer and the drug. Both approaches are illustrated in the Experimental section.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, alditol such as mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, the water-soluble, non-peptidic oligomer can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble and non-peptidic polymer includes $CH_3—(OCH_2CH_2)_n—$, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the tricyclic (in contrast to the step-wise addition of one or more monomers to effectively "grow" the oligomer onto the tricyclic), it is preferred that the composition containing an activated form of the water-soluble, non-peptidic oligomer be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., J. Org. Chem., 6870-6873 (1999), WO 02/098949, and U.S. Patent Application Publication 2005/0136031.

When present, the spacer moiety (through which the water-soluble, non-peptidic polymer is attached to the tricyclic) may be a single bond, a single atom, such as an oxygen atom or a sulfur atom, two atoms, or a number of atoms. A spacer moiety is typically but is not necessarily linear in nature. The spacer moiety, "X," is hydrolytically stable, and is preferably also enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH-C(O)—NH—). In selected embodiments, the linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) other atoms, as described further below.

More specifically, in selected embodiments, a spacer moiety of the invention, X, may be any of the following: "-" (i.e., a covalent bond, that may be stable or degradable, between the tricyclic residue and the water-soluble, non-peptidic oligomer), —O—, —NH—, —S—, —C(O)—, —C(O)O—, —OC(O)—, —CH₂—C(O)O—, —CH₂—OC(O)—, —C(O)O—CH₂—, —OC(O)—CH₂—, C(O)—NH, NH—C(O)—NH, O—C(O)—NH, —C(S)—, —CH₂—, —CH₂—CH₂—, —CH₂—CH₂—CH₂—, —CH₂—CH₂—CH₂—CH₂—, —O—CH₂—, —CH₂—O—, —O—CH₂—CH₂—, —CH₂—O—CH₂—, —CH₂—CH₂—O—, —O—CH₂—CH₂—CH₂—, —CH₂—O—CH₂—CH₂—, —CH₂—CH₂—O—CH₂—, —CH₂—CH₂—CH₂—O—, —O—CH₂—CH₂—CH₂—CH₂—, —CH₂—O—CH₂—CH₂—CH₂—, —CH₂—CH₂—O—CH₂—CH₂—, —CH₂—CH₂—CH₂—O—CH₂—, —CH₂—CH₂—CH₂—CH₂—O—, —C(O)—NH—CH₂—, —C(O)—NH—CH₂—CH₂—, —CH₂—C(O)—NH—CH₂—, —CH₂—CH₂—C(O)—NH—, —C(O)—NH—CH₂—CH₂—CH₂—, —CH₂—C(O)—NH—CH₂—CH₂—, —CH₂—CH₂—C(O)—NH—CH₂—, —CH₂—CH₂—CH₂—C(O)—NH—, —C(O)—NH—CH₂—CH₂—CH₂—CH₂—, —CH₂—C(O)—NH—CH₂—CH₂—CH₂—, —CH₂—CH₂—C(O)—NH—CH₂—CH₂—, —CH₂—CH₂—CH₂—C(O)—NH—CH₂—, —CH₂—CH₂—CH₂—CH₂—C(O)—NH—, —CH₂—CH₂—CH₂—C(O)—NH—CH₂—CH₂—, —CH₂—CH₂—CH₂—CH₂—C(O)—NH—NH—C(O)—CH₂—, —CH₂—NH—C(O)—CH₂—, —CH₂—CH₂—NH—C(O)—CH₂—, —NH—C(O)—CH₂—CH₂—, —CH₂—NH—C(O)—CH₂—CH₂, —CH₂—CH₂—NH—C(O)—CH₂—CH₂, —C(O)—NH—CH₂—, —C(O)—NH—CH₂—CH₂—, —O—C(O)—NH—CH₂—, —O—C(O)—NH—CH₂—CH₂—, —NH—CH₂—, —NH—CH₂—CH₂—, —CH₂—NH—CH₂—, —CH₂—CH₂—NH—CH₂—, —C(O)—CH₂—, —C(O)—CH₂—CH₂—, —CH₂—C(O)—CH₂—, —CH₂—CH₂—C(O)—CH₂—, —CH₂—CH₂—C(O)—CH₂—CH₂—, —CH₂—CH₂—C(O)—, —CH₂—CH₂—CH₂—C(O)—NH—CH₂—CH₂—NH—, —CH₂—CH₂—CH₂—C(O)—NH—CH₂—CH₂—NH—C(O)—, —CH₂—CH₂—CH₂—C(O)—NH—CH₂—CH₂—NH—C(O)—CH₂—, bivalent cycloalkyl group, —N(R⁶)—, R⁶ is H or an organic radical selected from the group consisting of alkyl, substituted alkyl, alkenyl, substituted alkenyl, alkynyl, substituted alkynyl, aryl and substituted aryl. Additional spacer moieties include, acylamino, acyl, aryloxy, alkylene bridge containing between 1 and 5 inclusive carbon atoms, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, and 4-(methoxy-lower alkyl)-1-piperizinyl.

For purposes of the present invention, however, a group of atoms is not considered a linkage when it is immediately adjacent to an oligomer segment, and the group of atoms is the same as a monomer of the oligomer such that the group would represent a mere extension of the oligomer chain.

The linkage "X" between the water-soluble, non-peptidic oligomer and the small molecule is typically formed by reaction of a functional group on a terminus of the oligomer (or nascent oligomer when it is desired to "grow" the oligomer onto the tricyclic) with a corresponding functional group within the tricyclic. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R$^1$). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: $CH_3O—(CH_2—CH_2—O)_n—(CH_2)_p—C(O)H$, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4.

The termini of the water-soluble, non-peptidic oligomer not bearing a functional group is capped to render it unreactive. When the oligomer includes a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative that reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the tricyclic may not have a functional group suited for conjugation. In this instance, it is possible to modify (or "functionalize") the "original" tricyclic so that it does have a functional group suited for conjugation. For example, if the tricyclic has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule tricyclic bearing a carboxyl group wherein the carboxyl group-bearing small molecule tricyclic is coupled to an amino-terminated oligomeric ethylene glycol, to provide a conjugate having an amide group covalently linking the small molecule tricyclic to the oligomer. This can be performed, for example, by combining the carboxyl group-bearing small molecule tricyclic with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule tricyclic bearing a hydroxyl group wherein the hydroxyl group-bearing small molecule tricyclic is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

Further, it is possible to prepare a conjugate of a small molecule tricyclic moiety bearing a hydroxyl group (such as, for example, the tricyclic moieties having structures encompassed within Formula I) wherein the hydroxyl group-bearing small molecule tricyclic moiety is coupled to an oligomeric ethylene glycol bearing an haloformate group [e.g., $CH_3(OCH_2CH_2)_nOC(O)$-halo, where halo is chloro, bromo, iodo] to result in a carbonate [—O—C(O)—O—] linked small molecule conjugate. This can be performed, for example, by combining a tricyclic moiety and an oligomeric ethylene glycol bearing a haloformate group in the presence of a nucleophilic catalyst (such as 4-dimethylaminopyridine or "DMAP") to thereby result in the corresponding carbonate-linked conjugate.

In another example, it is possible to prepare a conjugate of a small molecule tricyclic bearing a ketone group by first reducing the ketone group to form the corresponding hydroxyl group. Thereafter, the small molecule tricyclic now bearing a hydroxyl group can be coupled as described herein.

In still another instance, it is possible to prepare a conjugate of a small molecule tricyclic bearing an amine group. In one approach, the amine group-bearing small molecule tricyclic and an aldehyde-bearing oligomer are dissolved in a suitable buffer after which a suitable reducing agent (e.g., $NaCNBH_3$) is added. Following reduction, the result is an amine linkage formed between the amine group of the amine group-containing small molecule tricyclic and the carbonyl carbon of the aldehyde-bearing oligomer.

In another approach for preparing a conjugate of a small molecule tricyclic bearing an amine group, a carboxylic acid-bearing oligomer and the amine group-bearing small molecule tricyclic are combined, typically in the presence of a coupling reagent (e.g., DCC). The result is an amide linkage formed between the amine group of the amine group-containing small molecule tricyclic and the carbonyl of the carboxylic acid-bearing oligomer.

Exemplary compounds of the invention include those having the following structure:

Formula I-C

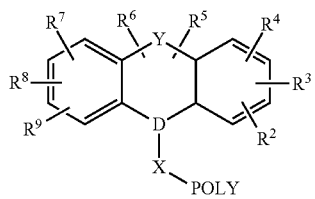

wherein:
D is C or N;
Y is selected from the group consisting of —$CH_2$—, —CH—, —$CH_2CH_2$—, —CH=CH—, —$CH_2$—S—, $CH_2$—O—, $CH_2$—NH—, —S—$CH_2$—, —O—$CH_2$—, —NH—$CH_2$—, —HN—, —O—, —N=C—, —C=N—, and —S—, unsubstituted or optionally substituted;
X is a spacer moiety; and
POLY is a water-soluble, non-peptidic oligomer.

The conjugates of the invention can exhibit a reduced blood-brain barrier crossing rate. Moreover, the conjugates maintain at least about 5%, 10%, 20%, 30%, 40%, 50%, 60%, 70%, or more of the bioactivity of the unmodified parent small molecule drug.

While it is believed that the full scope of the conjugates disclosed herein behave as described, an optimally sized oligomer can be identified as follows.

First, an oligomer obtained from a monodisperse or bimodal water soluble oligomer is conjugated to the small molecule drug. Preferably, the drug is orally bioavailable, and on its own, exhibits a non-negligible blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. Preferably, the compounds according to the invention maintain a significant degree of bioactivity relative to the parent drug, i.e., greater than about 30% of the bioactivity of the parent drug, or even more preferably, greater than about 50% of the bioactivity of the parent drug.

The above steps are repeated one or more times using oligomers of the same monomer type but having a different number of subunits and the results compared.

For each conjugate whose ability to cross the blood-brain barrier is reduced in comparison to the non-conjugated small molecule drug, its oral bioavailability is then assessed. Based upon these results, that is to say, based upon the comparison of conjugates of oligomers of varying size to a given small molecule at a given position or location within the small molecule, it is possible to determine the size of the oligomer most effective in providing a conjugate having an optimal balance between reduction in biological membrane crossing, oral bioavailability, and bioactivity. The small size of the oligomers makes such screenings feasible and allows one to effectively tailor the properties of the resulting conjugate. By making small, incremental changes in oligomer size and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

To determine whether the tricyclic or the conjugate of a tricyclic and a water-soluble non-peptidic polymer has activity as a tricyclic therapeutic, it is possible to test such a compound. The tricyclic compounds have sedative, hypnotic, anti-anxiety, tranquilizing, anticonvulsant, and muscle relaxant effects in mammals and birds. They also exhibit anti-depressant and analgesic actions in mammals.

In vitro binding studies to receptors using various cell lines have become routine in pharmaceutical industry.

Sedative effects: Chimney test: The test determines the ability of mice to back up and out of a vertical glass cylinder within 30 seconds. At an effective dosage, 50% of the mice will fail doing it ($ED_{50}$).

Dish test: Mice in Petri dishes (10 cm diameter, 5 cm high, partially embedded in wood shavings), climb out in a very short time, when not treated. Mice remaining in the dish for more than 3 minutes indicate tranquilization. $ED_{50}$ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than 1 minute. The $ED_{50}$ (intraperitoneal administration) is determined by identifying the amount of compound that causes 50% of the mice to stay on the pedestal.

Nicotine antagonism test: Mice in a group of 6 are injected with the test compound. Thirty minutes later the mice including control (untreated) mice are injected with nicotine salicylate (2 mg/kg). The control mice show over-stimulation, i.e., (1) running convulsions followed by (2) tonic extensor fits; followed by (3) death. The $ED_{50}$ (intraperitoneal administration) is determined by identifying the amount of compound that causes 50% of the mice to not show over-stimulation.

Antagonism to strychnine (as sulfate): The test consists of orally administering into mice the test compound, and 30 minutes later 3 mg/kg strychnine sulfate intraperitoneally. The survivors after 4 hours reflect the activity of the compound as a muscle relaxant and antispasmodic.

The main function of an anti-depressant is to return the depressed individual to normal functioning. This should be carefully differentiated from psychic stimulants such as the amphetamines which produce over-stimulation in the normal individual.

Many different methods have been and are used to evaluate antidepressant activity. In general these methods involve antagonism to a depressant such as reserpine or tetrabenazine or a synergistic increase of the toxicity of certain compounds (i.e. yohimbine or 3,4-dihydroxyphenylalanine) and comparison of the drug action of the new compound with other known antidepressants. No single test alone can determine whether or not a new compound is an antidepressant or not, but the profile evidenced by various tests will establish the anti-depressant action if present. A number of such tests are described below.

Hypothermic tests with oxotermorine: [1-(4-pyrrolidino-2-butynyl)-2-pyrrolidinone]. Oxotremorine (as well as apomorphine and tetrabenazine) produces hypothermic responses in mice. This response is blocked by anticholinergics and antidepressants such as atropine and imipramine respectively. Mice are injected intraperitoneally with 1 mg of oxotremorine. The lowering of the body temperature is measured rectally with an electronic thermometer, before and 30 minutes after drug administration. About four degree centigrade difference between the control mice (oxotremorine alone) and the treated mice (oxotremorine and test compound) is used to indicate the antagonistic action of the test compound.

Potentation of yohimbine aggregation toxicity: Mice are injected with the anti-depressant and 30 minutes later with 30 mg of yohimbine hydrochloride in saline solution. After two hours, the $LD_{50}$ are determined. Normally no mice are killed by 30 mg of yohimbine. If yohimbine is administered in the presence of an anti-depressant an increase of the toxicity of yohimbine is observed. The $ED_{50}$ value of the test compound is determined.

Potentiation of apomorphine gnawing: Mice are administered the test compound intraperitoneally one hour prior to the subcutaneous injection of apomorphine hydrochloride 10 mg/kg. The mice are then placed in a plastic box (6"×11'×5") lined at the bottom with a cellophane-backed, absorbent paper. The degree of damage to the paper at the end of 30 min is scored from zero to 4. The scores of 3 and 4 indicate that the compound is a potentiator of apomorphine in this test.

To determine whether the tricyclic derivative itself or the conjugate of tricyclic or a derivative thereof has activity (such as analgesic activity), it is possible to test such a compound. For example, the compound of interest can be administered to a mouse topically and analgesia assessed as described in Kolesnikov et al. (1999) *J. Pharmacol. Exp. Ther.* 290: 247-252. Briefly, the distal portion of the tail (2-3 cm) is immersed in a DMSO solution containing the compound of interest for the stated time, typically two minutes. Testing is performed on the portion of the tail immersed in the treatment solution, because the analgesic actions of agents administered in this manner are restricted to the exposed portions of the tail. Antinociception, or analgesia, is defined as a tail-flick latency for an individual animal that is twice its baseline latency or greater. Baseline latencies typically range from 2.5 to 3.0 seconds, with a maximum cutoff latency of 10 seconds to minimize tissue damage in analgesic animals. $ED_{50}$ values can be determined.

In another approach for evaluating analgesic activity of the tricyclic derivative itself or the conjugate of tricyclic or a derivative thereof, a "writhing test" can be conducted. Briefly, a 0.7% acetic acid solution is administered (i.p.) to a mouse and the numbers of writhing responses are counted for ten minutes. Thereafter, the compound to be tested is administered [by, for example, injection (e.g., subcutaneous injection)] to the mouse and antinociception is quantified as percent inhibition using the following formula: % inhibition=[(control responses-test responses)/control responses]× 100.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, maltitol, lactitol, xylitol, sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines, fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethylcellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that a reduction in first pass metabolism may be achieved relative to the parent drug. Such a result is advantageous for many orally administered drugs that are substantially metabolized by passage through the gut. In this way, clearance of the conjugate can be modulated by selecting the oligomer molecular size, linkage, and position of covalent attachment providing the desired clearance properties. One of ordinary skill in the art can determine the ideal molecular size of the oligomer based upon the teachings herein. Preferred reductions in first pass metabolism for a conjugate as compared to the corresponding nonconjugated small drug molecule include: at least about 10%, at least about 20%, at least about 30; at least about 40; at least about 50%; at least about 60%, at least about 70%, at least about 80% and at least about 90%.

Thus, the invention provides a method for reducing the metabolism of an active agent. The method comprises the steps of: providing monodisperse or bimodal conjugates, each conjugate comprised of a moiety derived from a small molecule drug covalently attached by a stable linkage to a water-soluble oligomer, wherein said conjugate exhibits a reduced rate of metabolism as compared to the rate of metabolism of the small molecule drug not attached to the water-soluble oligomer; and administering the conjugate to a patient. Typically, administration is carried out via one type of administration selected from the group consisting of oral administration, transdermal administration, buccal administration, transmucosal administration, vaginal administration, rectal administration, parenteral administration, and pulmonary administration.

Although useful in reducing many types of metabolism (including both Phase I and Phase II metabolism can be reduced), the conjugates are particularly useful when the small molecule drug is metabolized by a hepatic enzyme (e.g., one or more of the cytochrome P450 isoforms) and/or by one or more intestinal enzymes.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All non-PEG chemical reagents referred to in the appended examples are commercially available unless otherwise indicated. The preparation of PEG-mers is described in, for example, U.S. Patent Application Publication No. 2005/0136031.

All $^1$H NMR (nuclear magnetic resonance) data were generated by an NMR spectrometers. A list of certain compounds as well as the source of the compounds is provided below.

Example 1

Desipramine Small PEG Conjugation Derivatives

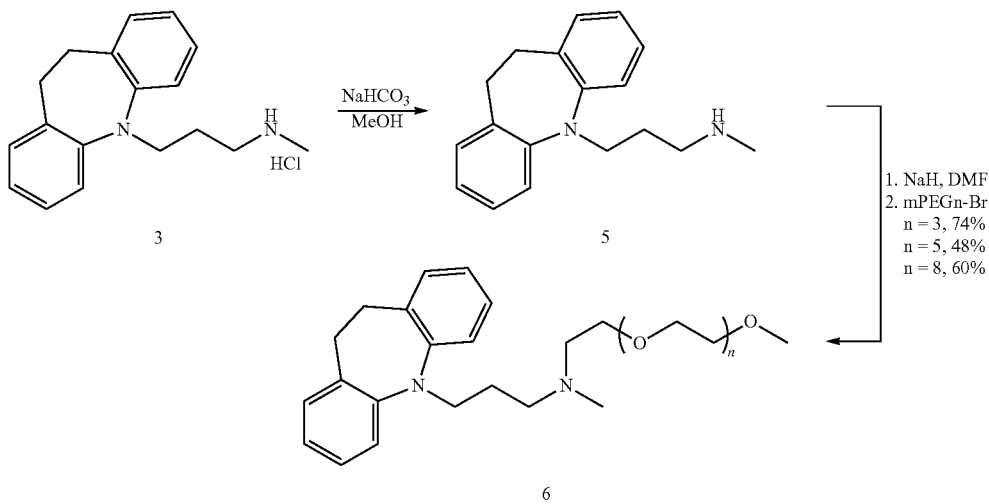

Desipramine, iminodibenzyl, sodium hydride (NaH), 1-bromo-3-chloropropane, lithium amide (LiNH$_2$) were purchased from Sigma-Aldrich (St Louis, Mo.). DCM was distilled from CaH$_2$. DMF (anhydrous), toluene (anhydrous), and other organic solvents were used as they purchased.

Desipramine (2.00 g, 6.60 mmol) was dissolved in methanol (40 mL) and saturated NaHCO$_3$ (80 mL). The reaction was kept at room temperature for 30 min and the solution pH was >10. After the methanol was removed under reduced pressure, the aqueous solution was extracted with DCM (50 mL+25 mL×2). The combined organic layers were dried over Na$_2$SO$_4$, filtered, and the solvent removed under reduced pressure. The resulting residue was solidified overnight by vacuum drying and a yellowish sample (1.79 g, >100% yield) was obtained.

The above free desipramine (170 mg, 0.64 mmol) was dissolved in DMF (3.2 mL). NaH (46 mg, 1.92 mmol, 3 eq) was added and the reaction was kept at room temperature for 5 min. mPEG$_3$-Br (283 µL, 1.28 mmol, 2 eq) was added and the reaction was allowed to stir overnight (16 h). Upon obtaining a clear solution, the reaction was quenched with NH$_4$Cl (50 mL) and extracted with DCM (15 mL×3). The organic phases were combined and dried over Na$_2$SO$_4$. After filtration, DCM was evaporated and DMF was rotavapped under high vacuum. The resulting residue was loaded onto a Biotage 12M column and purified with 2-20% methanol in DCM within 15 CV. The product was monitored under 254 nm and collected (194.7 mg, 74% yield). A mixture of product and starting material was also collected and saved.

mPEG$_5$-Br and mPEG$_8$-Br were used for the other desipramine derivative syntheses using a similar procedure. The product quality was characterized with NMR, analytical-HPLC and identified by LC-MS/MALDI.

Desipramine (5)

$^1$H NMR (300 MHz, CDCl$_3$) δ 1.77 (2H, q, J=6.9 Hz), 2.37 (3H, s), 2.61 (2H, t, J=6.9 Hz), 3.16 (3H, s), 3.79 (2H, t, J=6.9 Hz), 6.91 (2H, dt, J=2.1, 7.5 Hz), 7.07-7.12 (6H, m).

mPEG$_3$-desipramine (6a) (n=3)

R$_f$=0.36 (DCM:MeOH=10:1), RP-HPLC (betasil C18, 0.5 mL/min, 10-80% ACN in 10 min) 6.49 min, MALDI (MH$^+$) 413.3; $^1$H NMR (300 MHz, CDCl$_3$) δ 1.73 (2H, bs), 2.19 (3H, bs), 2.44 (2H, bs), 2.51 (2H, bs), 3.15 (4H, s), 3.37 (3H, s), 3.51-3.66 (10H, m), 3.76 (2H, t, J=6.6 Hz), 6.90 (2H, dt, J=1.2, 7.5 Hz), 7.06-7.15 (6H, m).

mPEG$_5$-desipramine (6b) (n=5)

R$_f$=0.34 (DCM:MeOH=10:1), RP-HPLC (betasil C18, 0.5 mL/min, 10-80% ACN in 10 min) 8.31 min, MALDI (MNa$^+$) 523.3; $^1$H NMR (300 MHz, CDCl$_3$) δ 1.74 (2H, bs), 2.18 (3H, bs), 2.43 (2H, bs), 2.50 (2H, bs), 3.15 (4H, s), 3.38 (3H, s), 3.49-3.66 (18H, m), 3.76 (2H, t, J=6.6 Hz), 6.90 (2H, dt, J=1.2, 7.5 Hz), 7.06-7.15 (6H, m).

mPEG$_8$-desipramine (6c) (n=8)

R$_f$=0.32 (DCM:MeOH=10:1), RP-HPLC (betasil C18, 0.5 mL/min, 10-80% ACN in 10 min) 8.35 min, MALDI (MNa+) 655.5; NMR (300 MHz, CDCl3) δ 1.74 (2H, bs), 2.18 (3H, bs), 2.43 (2H, bs), 2.51 (2H, bs), 3.15 (4H, s), 3.37 (3H, s), 3.38 (3H, s), 3.52-3.66 (30H, m), 3.76 (2H, t, J=6.6 Hz), 6.90 (2H, dt, J=1.2, 7.5 Hz), 7.06-7.15 (6H, m).

Total Synthesis of Secondary Amine Derivatives

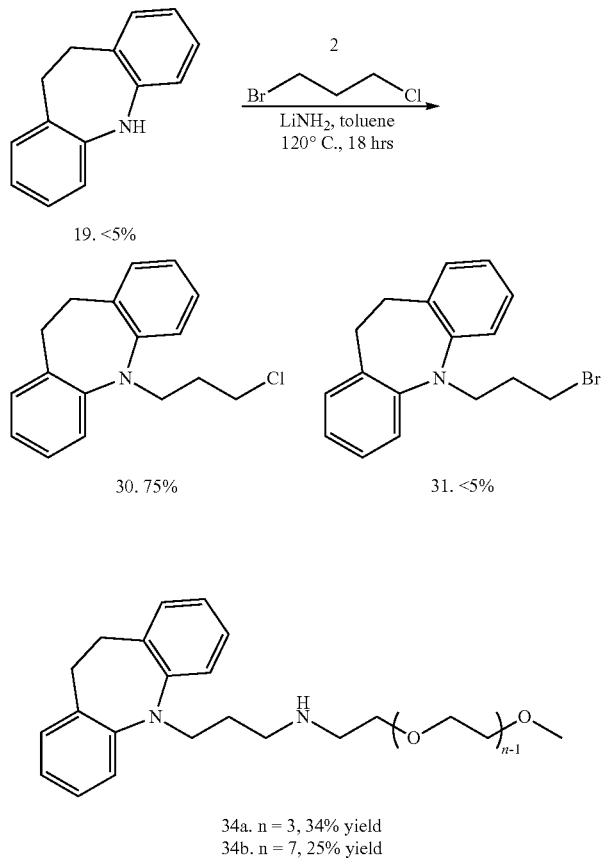

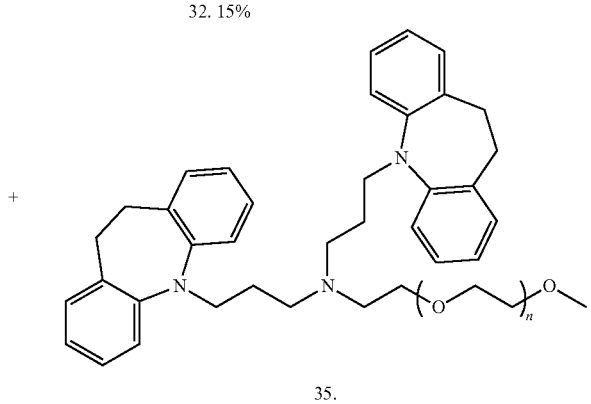

In a MCE microwave reaction tube, iminodibenzyl (1.95 g, 10 mmol) was suspended in toluene (10 mL). The solution was protected under N2. After 1-bromo-3-chloropropane (1.48 mL, 15 mmol) was added, the solution became clear at room temperature. LiNH2 (276 mg, 12 mmol) was then added and the tube was sealed. The microwave reaction was carried out at 120° C. over 18 hrs. The reaction was quenched with a saturated aqueous NaHCO3 solution and extracted with EtOAc (50 mL×2). The combined organic phases were dried over MgSO4 and the solvent removed under reduced pressure. The resulting residue was loaded onto a Biotage 25M column and eluted with 1-6% of EtOAc in Hexane over 15 CV. A pure sample fraction was used to run NMR and all other fraction mixtures were combined. A slight yellowish product (2.57 g, 95% yield) was collected after overnight drying under high vacuum.

mPEG7-desipramine

The above iminodibenzyl alkylation product mixture (325 mg, 1.2 mmol) was added to a microwave reaction tube together with mPEG7-NH2 (340 µL, 1.0 mmol). K2CO3 (207 mg, 1.5 mmol) was added with H2O (1 mL). The starting material was suspended at the top layer of the water phase—stirring was difficult before heating occurred. The microwave reaction was carried out at 120° C. over 2 hrs. The reaction was monitored by TLC for the disappearance of mPEG-NH2. The reaction was then diluted with an aqueous NaHCO3 solution and extracted with DCM (10 mL×3). The combined organic phases were dried over MgSO4, filtered, and the solvent removed under reduced pressure. The resulting residue was loaded onto a Biotage 25M column and purified with eluting 2-18% methanol in DCM over 20 CV. A colorless product (193 mg, 34% yield) was collected after overnight drying. The desired product was identified by NMR and LC-MS and analytical-HPLC indicated the purity to be over 98%.

mPEG3-desipramine

The reaction was carried out in a similar manner as above. However, the product mixture contained a nearly 1:1 ratio of mono- to di-alkylation products which were inseparable by TLC. Purification by Biotage Flash Chromatography (12M reverse phase column, 25-100% CAN in 16 CV) gave the desired product (187 mg, 25% yield) with over 98% purity.

5-(3-Chloro-propyl)-10,11-dihydro-5H-dibenzo[b,f]azepine (30)

Rf=0.22 (Hex:EtOAc=16:1), RP-HPLC (betasil C18, 0.5 mL/min, 10-80% ACN in 10 min) 9.55 min, LC-MS (ESI, MH+) 272.2; 1H NMR (300 MHz, CDCl3) δ 2.04 (2H, q, J=6.6 Hz), 3.16 (4H, s), 3.57 (2H, t, J=6.3 Hz), 3.90 (2H, t, J=6.3 Hz), 6.93 (2H, dt, J=1.2, 6.9 Hz), 7.07-7.16 (6H, m).

N-mPEG$_3$-3-(10,11-dihydro-dibenzo[b,f]azepin-5-yl)-propylamine (34a)

R$_f$=0.43 (DCM:MeOH=10:1), RP-HPLC (betasil C18, 0.5 ml/min, 10-80% ACN in 10 min) 6.49 min, LC-MS (ESI, MH$^+$) 399.3; $^1$H NMR (300 MHz, CDCl$_3$) δ 2.05-2.13 (2H, m), 3.05 (4H, bs), 3.15 (4H, s), 3.31 (3H, s), 3.43-3.52 (6H, m), 3.60-3.64 (2H, m), 3.76 (2H, t, J=6.0 Hz), 3.85 (2H, t, J=6.0 Hz), 6.94 (2H, t, J=7.4 Hz), 7.04-7.17 (6H, m).

N-mPEG$_7$-3-(10,11-dihydro-dibenzo[b,f]azepin-5-yl)-propylamine (34b)

R$_f$=0.45 (DCM:MeOH=10:1), RP-HPLC (betasil C18, 0.5 mL/min, 10-80% ACN in 10 min) 6.39 min, LC-MS (ESI, MH$^+$) 575.4; $^1$H NMR (300 MHz, CDCl$_3$) δ 1.92-1.96 (2H, m), 2.81-2.88 (4H, m), 3.14 (4H, s), 3.36 (3H, s), 3.51-3.67 (26H, m), 3.81 (2H, t, J=6.3 Hz), 2H, t, J=7.2 Hz), 7.05-7.14 (6H, m).

pKa and LogP Determinations:

| Molecule | pKa | LogP |
| --- | --- | --- |
| Desipramine | 9.72 | 3.32 |
| mPEG$_3$-N-Desipramine | 8.47 | 3.41 |
| mPEG$_5$-N-Desipramine | 8.55 | 3.11 |
| mPEG$_8$-N-Desipramine | 8.66 | 2.77 |
| mPEG$_3$-NH-Desipramine | 8.96 | 3.14 |
| mPEG$_7$-NH-Desipramine | 8.94 | 2.5 |

Example 2

Synthesis of mPEG-n-Carbamazepine

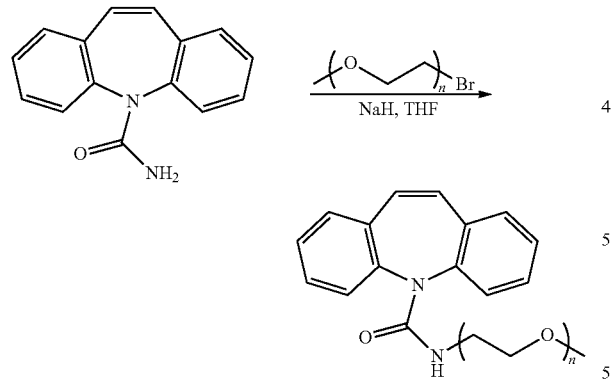

n = 3, 5, 7

Carbamazepine (118 mg, 0.5 mmol) was dissolved in 5 ml THF, and NaH (60%, 60 mg, 1.5 mmol) was added to the solution. The mixture was stirred for 5 min. before mPEG-Br [n=3, 5, 7] (0.6 mmol) was added. The resulting mixture was stirred at r.t. for 14 h. The solid was removed and 150 ml dichloromethane was added. The organic phase was washed with H$_2$O (2×150 mL), dried over Na$_2$SO$_4$ and solvent was removed under reduced pressure. The crude product was purified by column chromatography (Biotage Flash Chromatography System, [A: MeOH, 1-4% (20CV), 4-6% (10CV), B: DCM]. The desired product was obtained as sticky oil (yield: 60-80%).

mPEG$_3$-N-Carbamazepine $^1$H NMR (300 MHz, CDCl$_3$): δ 7.48-7.31 (m, 8H), 6.92 (s, 2H), 3.59 (m, 2H), 3.53 (m, 6H), 3.46 (m, 2H), 3.38 (s, 3H), 3.34 (m, 2H). LC-MS: 383.2 (M+H)$^+$.

mPEG$_5$-N-Carbamazepine $^1$H NMR (300 MHz, CDCl$_3$): δ 7.48-7.31 (m, 8H), 6.92 (s, 2H), 3.66-3.54 (m, 16H), 3.45 (m, 2H), 3.38 (s, 3H), 3.33 (m, 2H). LC-MS: 471.2 (M+H)$^+$.

mPEG$_7$-N-Carbamazepine $^1$H NMR (300 MHz, CDCl$_3$): δ 7.48-7.31 (m, 8H), 6.92 (s, 2H), 3.66-3.55 (m, 18H), 3.54-3.51 (m, 6H), 3.44 (m, 2H), 3.38 (s, 3H), 3.31 (m, 2H). LC-MS: 559.3 (M+H)$^+$.

Example 3

Synthesis of mPEG$_n$-N-Amitriptyline Conjugates

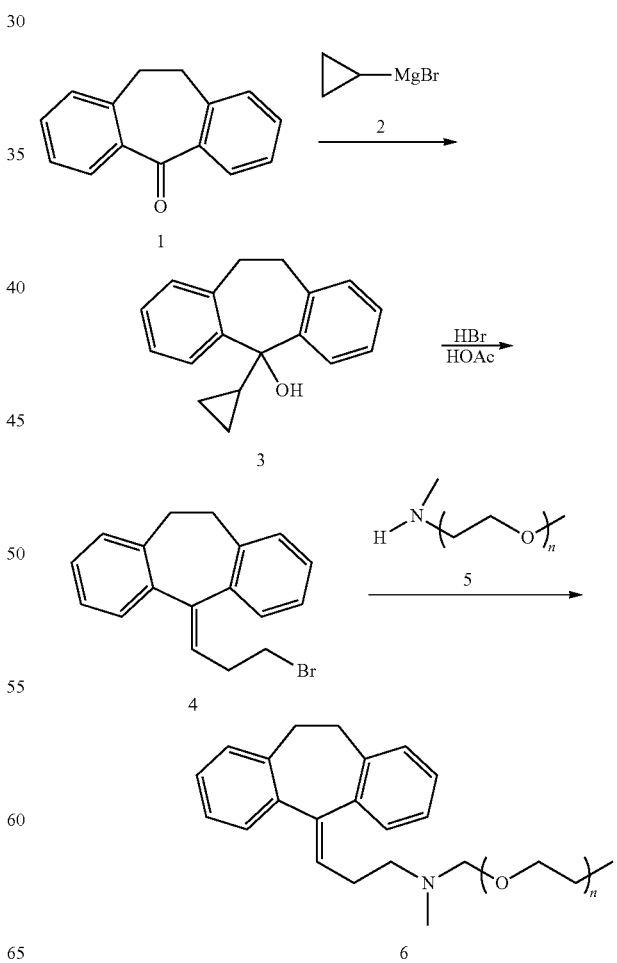

Synthesis of 5-Cyclopropyl-10,11-dihydro-5H-dibenzo[a,d]cyclohepten-5-ol (3)

In a three neck round bottom flask equipped with stirrer, (0.243 g, 0.009 mol) of magnesium turnings and 2.5 mL of dry THF was added. The reaction was stirred to allow the metal to dissolve. At this point the temperature was raised to 60° C. and cyclopropyl bromide (1.21 g, 0.010 mol) was added dropwise. The reaction mixture was allowed to reflux for 1.5 h at 70° C. and then lowered to 60° C. Then (1.04 g, 0.005 mol) of 10,11-dihydro-dibenzo[a,d]cyclohepten-5-one was added dropwise. Upon addition, the solution turned purple in color. The temperature was raised to 70° C. after addition was complete. The reaction refluxed for an additional 2 h and HPLC was used to monitor reaction progress. Ammonium chloride/H$_2$O (7.5 mL) was added to quench the reaction and the flask placed in an ice bath. The resulting solution was filtered and the filtrate was transferred to a 250-mL separatory funnel charged with DCM (100 mL). Then finally NaCl/H$_2$O solution (80 mL) was added. The organic phase was removed and dried over Na$_2$SO$_4$ for 2 h. The solvent was removed under reduced pressure and the product was dried under vacuum overnight. $^1$H NMR and LC/MS confirmed the product. (Yield~52%).

Synthesis of -5-(3-Bromo-propylidene)-10,11-dihydro-5H-dibenzo[a,d]cycloheptene (4)

In a 100-mL round bottom flask, 5-cyclopropyl-10,11-dihydro-5H-dibenzo[a,d]cycloheptene-5-ol (0.130 g, 0.0006 mol) was added with 1 mL acetic acid. The solid was allowed to dissolve at which point the reaction mixture was chilled to 10° C. Then a solution of 33% hydrobromic acid (0.5 mL hydrobromic acid and 0.5 mL acetic acid; total 1 mL) was added to the flask. The reaction was allowed to stir for an additional 30 min. while reaction progress was monitored by HPLC. Then the reaction mixture was transferred to a separatory funnel and DCM (100 mL) added. The organic layer collected and washed with H$_2$O (1×100 mL) and dried over Na$_2$SO$_4$ for 2 hrs. The resulting product was purified by flash column chromatography on silica gel using MeOH/DCM (Biotage 25M column). The product was confirmed by $^1$H NMR and LC/MS. (Yield~62%).

Synthesis of mPEG$_n$-N-Amitriptyline (6)

In a 100-mL round bottom flask (0.120 g, 0.0004 mol) of 5-(3-bromo-propylidene)-10,11-dihydro-5H-dibenzo[a,d]cycloheptene with acetone (1 mL) was mixed until the solid completely dissolved. Then (0.137 g, 0.0008 mol) of mPEG$_n$-methyl amine was added. Finally (0.267 g, 0.002 mol) of K$_2$CO$_3$ was added with acetone (5 mL). The reaction mixture was heated to 70° C. reflux. After 8 h the reaction was checked for completion by HPLC. After cooling DCM (100 mL) was added to the flask and the resulting solution placed in a separatory funnel. The organic layer was removed and washed with NaCl/H$_2$O solution (1×100 mL) and dried over Na$_2$SO$_4$ for 2 hrs. The resulting product was purified by flash column chromatography on silica gel using MeOH/DCM (Biotage 25M column) to afford the desired product. (Yield~13-20%).

mPEG$_3$-N-Amtriptyline $^1$H-NMR (300 MHz, DMSO-d$_6$) δ 7.24-7.02 (m, 8H), 5.79 (t, 1H), 3.50-3.41 (m, 10H), 3.18 (s, 3H), 2.75 (br, 4H), 2.41-2.55 (m, 5H), 2.13 (br, 2H), 2.04 (s, 3H); LC-MS: Calc. 409.4. Found 410.4 (MH$^+$).

mPEG$_5$-N-Amtriptyline $^1$H-NMR (500 MHz, DMSO-d$_6$): δ 7.22-7.14 (m, 8H), 5.85 (t, 1H), 3.50-3.45 (m, 20H), 3.23 (s, 3H), 2.90 (br, 4H), 2.51-2.50 (m, 5H), 2.41 (br, 2H), 2.01 (s, 3H); LC-MS: Calc. 497.4. Found 498.4 (MH$^+$).

mPEG$_6$-N-Amtriptyline $^1$H-NMR (500 MHz, DMSO-d$_6$): δ 7.21-7.12 (m, 8H), 5.82 (t, 1H), 3.51-3.43 (m, 2H), 3.23 (s, 3H), 2.90 (br, 4H), 2.51-2.50 (m, 5H), 2.41 (br, 2H), 2.07 (s, 3H); LC-MS: Calc. 541.4. Found 542.3 (MH$^+$).

mPEG$_7$-N-Amtriptyline $^1$H-NMR (500 MHz, DMSO-d$_6$): δ 7.35-7.15 (m, 8H), 5.90 (t, 1H), 3.51-3.29 (m, 28H), 3.23 (s, 3H), 2.86 (br, 4H) 2.79-2.42 (m, 5H), 2.36 (br, 2H), 2.10 (s, 3H); LC-MS: Calc. 585.4. Found 586.3 (MH$^+$).

Example 4

PEG-Doxepin Synthesis

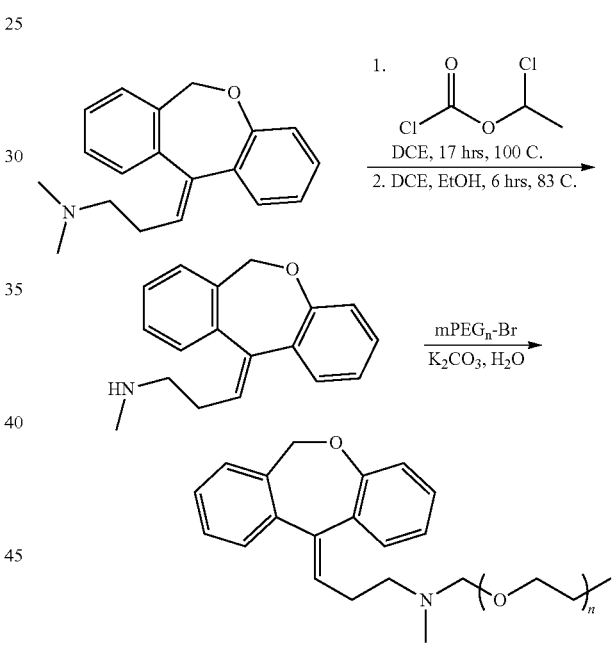

PEG-Doxepin Synthesis (Another Approach):

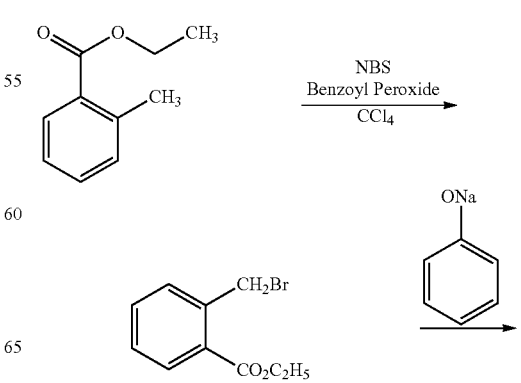

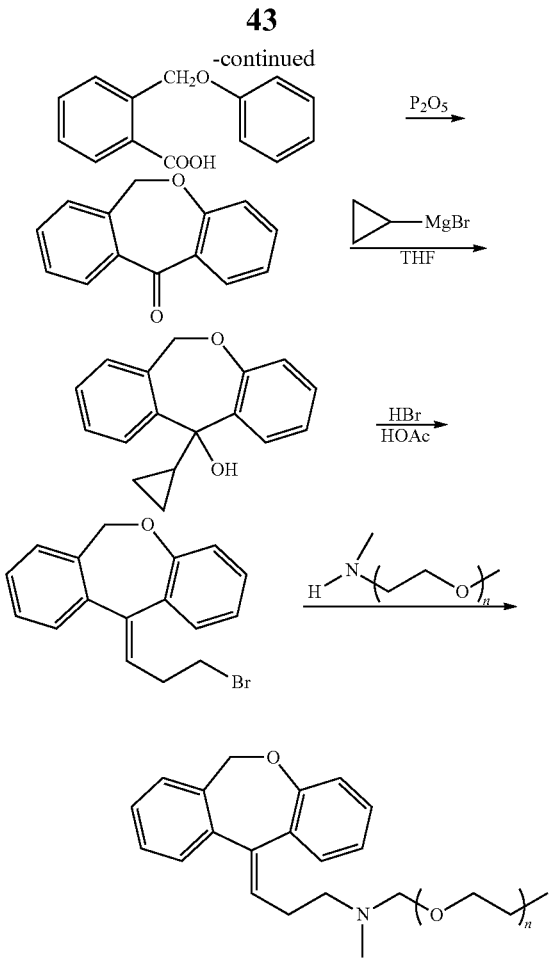

Example 5

Histamine Receptor Binding Assay

The receptor binding affinities of amitriptyline and four mPEG conjugates were evaluated using radioligand binding assays in membranes prepared from CHO cells that express the recombinant human H1, H2, H3 or H4 histamine receptors.

Competition binding experiments were conducted by incubating membranes with a fixed concentration of radioligand in the presence of variable concentrations of test compounds. The radioligands used were specific for each receptor subtype and the assay conditions are described in Table 2. Following incubations, the membranes were washed and the bound radioactivity was measured. Non-specific binding was measured in the presence of excess unlabelled ligand; this value was subtracted from the total binding yielding the specific binding at each test compound concentration.

$IC_{50}$ values were obtained from non-linear regression analysis of dose-response curves and were calculated only for those compounds that showed >50% inhibition of binding at the highest concentration tested. $K_i$ was obtained using the Cheng Prusoff correction using experimental $K_d$ values that were previously determined under the same assay conditions.

The binding affinities of amitriptyline and mPEG-amitriptyline conjugates are shown in Table 1. Amitriptyline and PEG-amitriptyline conjugates displayed high affinity binding to the H1 receptor. PEG conjugation resulted in less than 20-fold reduction in binding affinity, and this effect was PEG size dependent.

Binding affinity at the H2 receptor was nearly 3 orders of magnitude lower than that at the H1 receptors for all the molecules tested. mPEG conjugation also resulted in a reduction in binding affinity at the H2 receptors, and this effect was also PEG size dependent.

$K_i$ values could not be determined for the mPEG-6 and mPEG-7 amitriptyline at the H2 receptors, since >50% inhibition could not be observed at the highest concentration tested. The loss in binding affinity at the H2 receptor (>63-fold versus parent) was greater than the loss in binding affinity at the H1 receptor (<23-fold versus parent) suggesting that mPEG conjugation increased the H1:H2 receptor selectivity, making the mPEG-amitriptyline conjugates more selective for H1 receptors. No measurable binding to the H3 and H4 receptors was detected at the highest concentrations tested. The receptor binding selectivity for amitriptyline and mPEG-amitriptyline conjugates was H1>>>H2>H3=H4.

TABLE 1

Summary of Binding Affinity

| Test Compound | MW (Da) | H1 Receptor Ki (nM) | H1 Receptor Fold-change over parent | H2 Receptor Ki (nM) | H2 Receptor Fold-change over parent | H1:H2 Selectivity |
|---|---|---|---|---|---|---|
| Amitriptyline | 313.9 | 0.324 | 1 | 208 | 1 | 642 |
| mPEG3-N-Amitriptyline | 409.0 | 1.81 | 6 | 3010 | 14 | 1663 |
| mPEG5-N-Amitriptyline | 497.0 | 3.57 | 11 | 13100 | 63 | 3670 |
| mPEG6-N-Amitriptyline | 541.0 | 6.13 | 19 | Not obtained | — | — |
| mPEG7-N-Amitriptyline | 585.0 | 7.44 | 23 | Not obtained | — | — |

$K_i$ values at the H3 and H4 receptors could not be determined since <50% inhibition of radioligand binding was obtained at the highest concentration tested.

TABLE 2

Assay Conditions
Receptor source: Human recombinant CHO or CHO K1 cells expressing individual histamine H1, H2, H3, or H4 receptors.

| Receptor | Radioligand | Non-specific binding | Methods | Test Concentration |
|---|---|---|---|---|
| Histamine H1 | [³H]-Pyrilamine (1.2 nM) | Pyrilamine (1 μM) | Reaction in 50 mM Tris-HCl (pH 7.4), 2 mM | 0.01, 0.1, 0.3, 1, 3, 10, 30, 100 nM, |

TABLE 2-continued

Assay Conditions
Receptor source: Human recombinant CHO or CHO K1 cells
expressing individual histamine H1, H2, H3, or H4 receptors.

| Receptor | Radioligand | Non-specific binding | Methods | Test Concentration |
|---|---|---|---|---|
| | | | $MgCl_2$, 100 mM NaCl and 250 mM Sucrose at 25° C. for 3 h. | 3, 30 µM |
| Histamine H2 | [$^{125}$I]-Aminopotentidine (0.1 nM) | Tiotidine (3 µM) | Reaction in 50 mM phosphate (pH 7.4) at 25° C. for 2 h. | 0.01, 0.1, 0.3, 1, 3, 10, 30, 100 nM, 3, 30 µM |
| Histamine H3 | [$^3$H]-R(−)-α-Methyl-histamine (3 nM) | R(−)-α-Methyl-histamine (1 µM) | Reaction in 50 mM Tris-HCl (pH 7.4), 5 mM $MgCl_2$, 0.04% BSA at 25° C. for 1.5 h. | 0.01, 0.1, 0.3, 1, 3, 10, 30, 100 nM, 3, 30 µM |
| Histamine H4 | [$^3$H]-Histamine (8.2 nM) | Histamine (1 µM) | Reaction in 50 mM Tris-HCl (pH 7.4), 1.25 mM EDTA at 25° C. for 1.5 h. | 0.01, 0.1, 0.3, 1, 3, 10, 30, 100 mM, 3, 30 µM |

Example 6

Sodium Channel Assay

Carbamazepine and three its conjugates' effects on sodium channels were evaluated in vitro to determine their blocking properties using the whole-cell patch clamp method in isolated cardiac (human atrial myocytes) and neuronal (rat dorsal root ganglion) cells.

Human myocytes were obtained from specimens of human right atrial appendage obtained during surgery from hearts of patients undergoing cardiopulmonary bypass. The procedure produced rod-shaped, ion tolerant cells which were used within 24 hours after isolation (Crumb et al., 1995, *Am J Physiol* 268:H1335-H1342).

Dorsal root ganglion neurons were prepared from rats, post-natal day 14-18 (Blair and Bean, 2002, *J Neurosci* 22:10277-10290). Animals were anesthetized with isoflurane, decapitated, and ganglia were removed. Pieces of ganglia were treated to produce individual cells that were used within 48 hours after isolation.

The whole-cell patch clamp technique was carried out at 23±1° C. with precise micromanipulation under high power visual magnification to measure sodium currents. Glass pipettes were fire polished to produce tip diameters of 1-4 µm. The tip of the pipette, filled with electrolyte "internal" solution (a composition of (mM): 115 CsF, 20 CsCl, 10 NaF, 10 HEPES, 5 EGTA; pH adjusted to 7.2 with CsOH) was positioned onto a cell. The cell was in a bathing "external" solution (consisting of (mM): 115 TMA chloride, 10 NaCl, 5 CsCl, 1.8 $CaCl_2$, 1.2 $MgCl_2$, 10 HEPES, 11 dextrose, pH adjusted to 7.4 with TMA-OH). Pipette tip resistance was approximately 1.0 to 2.0 MD when filled with the internal solution. Suction was then applied to the pipette interior to seal the cell membrane onto the tip. Another suction pulse then broke the membrane, establishing electrical access into the interior of the cell. The cellular interior then became dialyzed by the solution the patch pipette was filled with.

After rupture of the cell membrane (entering whole-cell mode), current kinetics and amplitudes were allowed to stabilize (currents elicited by a series of voltage pulses given at 0.1 Hz were superimposed), as the cell was dialyzed with internal solution and paced at 1 Hz (3-5 minutes). Sodium current ($I_{Na}$) was measured using a voltage pulse to −20 mV (40 ms pulse duration) from a holding potential of −120 mV. Peak inward current was measured for $N_a$. Pacing rates of 0.1 and 3 Hz were examined. Test article, at concentrations of 0.1, 1, 3, 10, 30, and 100 µM, was added in a cumulative manner to a cell. Stock solutions of all compounds were prepared in DMSO at a concentration of 10 mM. To test for cell sensitivity, 1 µM TTX (tetrodotoxin) was added after exposure to test article. Exposure of 2 cardiac cells to TTX resulted in 47.2 and 56.8% reduction of $I_{Na}$. Exposure of 2 neuronal cells to TTX resulted in 93.2 and 96.8% reduction of $I_{Na}$.

Currents and voltages were recorded with patch-clamp amplifiers (Axopatch 1-B, Axon Instruments). Creation of voltage clamp pulses and data acquisition was controlled by a computer using electrophysiology software (pCLAMP version 9.2, Axon Instruments, now MDS, Sunnyvale, Calif.). Data was presented as % reduction of current amplitude, measured as current reduction after a steady-state effect had been reached in the presence of test article relative to current amplitude before introduction of test article (control). Each cell served as its own control.

Approximate $IC_{50}$ values (Table 3) were obtained from non-linear regression analysis of dose-response curves, using GraphPad's Prism 5.01 software, for cardiac and neuronal $I_{Na}$. Alternatively, data were analyzed for mean percent inhibition±SEM at the highest concentration tested (100 µM) where >50% inhibition of $I_{Na}$ could not be obtained.

Figure 2:
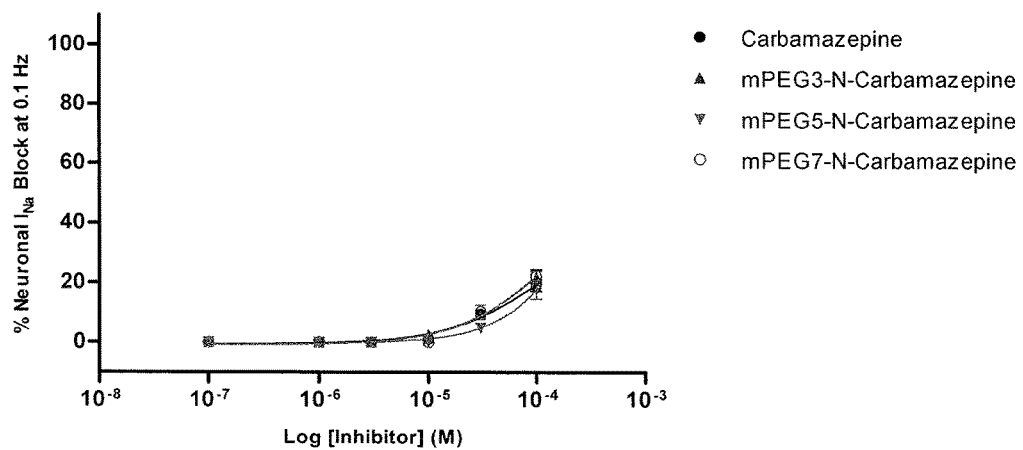
FIG. 2 shows blocking effects of carbamazepine and its conjugates on sodium current at 0.1 Hz (A) vs. 3 Hz (B) in isolated rat dorsal root ganglion cells. Data are mean±SEM.
Figure 2:
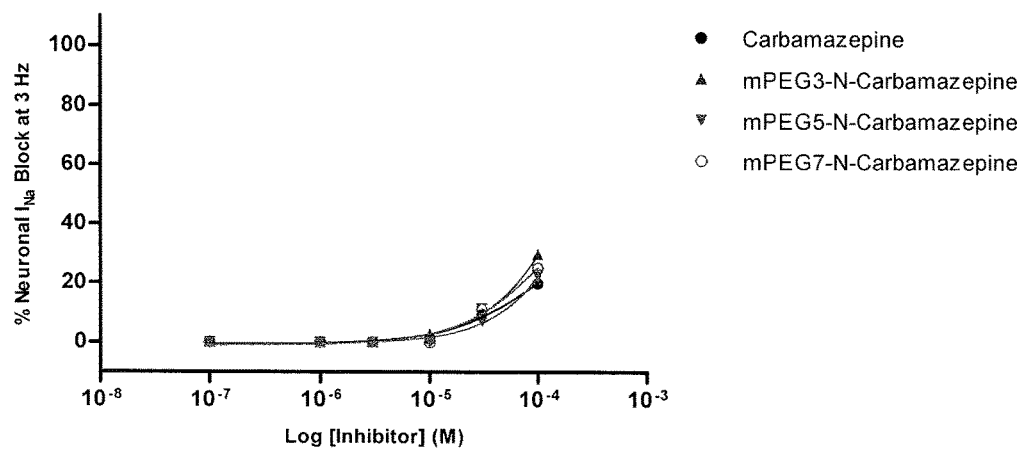
Figure 3:
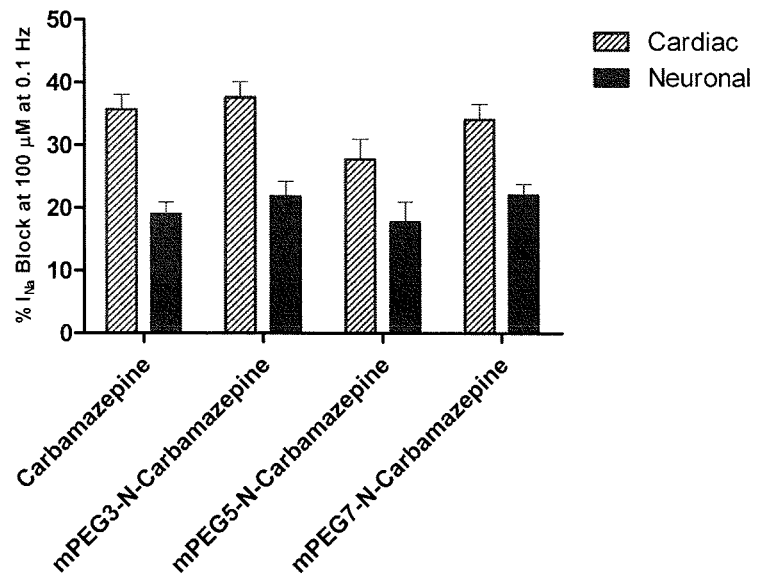
FIG. 3 shows mean (±SEM) percent sodium current block at 100 µM at 0.1 Hz (A) and 3 Hz (B) in isolated cardiac and neuronal cells for carbamazepine and its conjugates.
Figure 3:
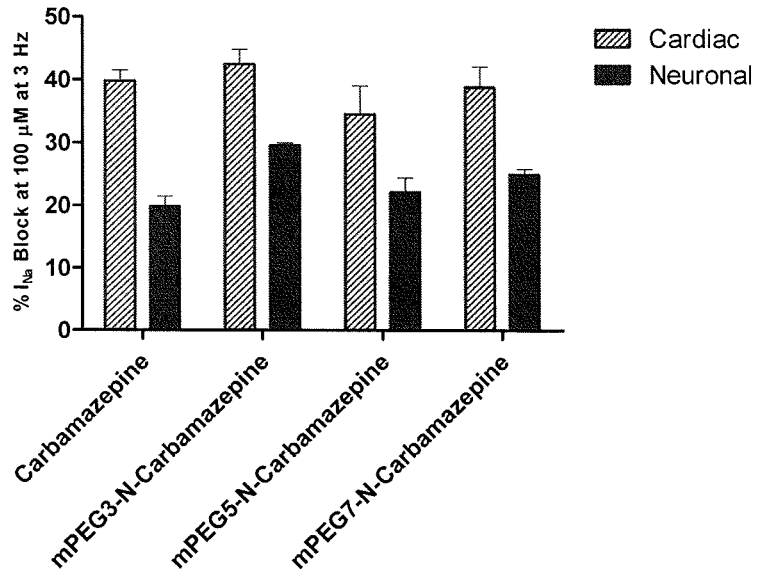

Carbamazepine and its PEG conjugates were tested for rate-dependent inhibition of cardiac and neuronal sodium channels. All PEG conjugates had similar activity as the parent compound at both cardiac (FIG. 1) and neuronal (FIG. 2) sodium channels. Under the conditions of the assay, all test articles produced incomplete block of sodium channels and a reliable $IC_{50}$ could not be obtained when concentrations up to 100 µM were used. All test articles exhibited a lower affinity for neuronal $I_{Na}$ versus cardiac $I_{Na}$ (FIG. 3); the response of the parent compound was consistent with published reports demonstrating that carbamazepine has a lower affinity for neuronal $I_{Na}$ versus cardiac $I_{Na}$. The data suggest that PEG conjugation does not alter the intrinsic pharmacology of the parent carbamazepine at cardiac and neuronal sodium channels.

TABLE 3

Summary of sodium channel blocking effects of carbamazepine series.

| Test Compound | MW (Da) | Cardiac $I_{Na}$ | | | | Neuronal $I_{Na}$ | | | |
|---|---|---|---|---|---|---|---|---|---|
| | | $IC_{50}$ at 0.1 Hz (M) | Fold Change Relative to Parent | $IC_{50}$ at 3 Hz (M) | Fold Change Relative to Parent | $IC_{50}$ at 0.1 Hz (M) | Fold Change Relative to Parent | $IC_{50}$ at 3 Hz (M) | Fold Change Relative to Parent |
| Carbamazepine | 236.3 | 1.6E−04 | 1.0 | 1.45E−04 | 1.0 | 1.02E−04 | 1.0 | 1.14E−04 | 1.0 |
| mPEG3-N-Carbamazepine | 382.5 | 4.6E−04 | 2.8 | 2.14E−04 | 1.5 | 1.42E−04 | 1.4 | 5.78E−04 | 5.1 |
| mPEG5-N-Carbamazepine | 470.6 | 6.1E−05 | 0.4 | 5.20E−05 | 0.4 | N/A | N/A | N/A | N/A |
| mPEG7-N-Carbamazepine | 558.7 | 3.8E−04 | 2.4 | 1.69E−04 | 1.2 | 1.44E−04 | 1.4 | 1.63E−04 | 1.4 |

$IC_{50}$ values are approximate as >50% inhibition was not obtained at the highest concentration tested.
N/A = Curve not generated based on data points.

Example 7

Noradrenalin Transporter Binding Assay

The binding affinities of desipramine and five PEG conjugates were evaluated using radioligand binding assays in membranes prepared from rat forebrain which express noradrenalin transporters.

Competition binding experiments were conducted by incubating membranes with 1.0 nM of radioligand, [$^3$H]-nisoxetine, in the presence of variable concentrations (0.1 nM to 3 μM and 3 nM to 100 μM for parent and PEG conjugates, respectively) of test compounds. The reaction was carried out in 50 mM Tris-HCl (pH 7.4), 300 mM NaCl, 5 mM KCl at 0-4° C. for 4 hours. Following incubations, the membranes were washed, and the bound radioactivity was measured. Non-specific binding was measured in the presence of excess desipramine (1.0 μM) as the cold ligand; this value was subtracted from the total binding to yield the specific binding at each test compound concentration.

Figure 4:
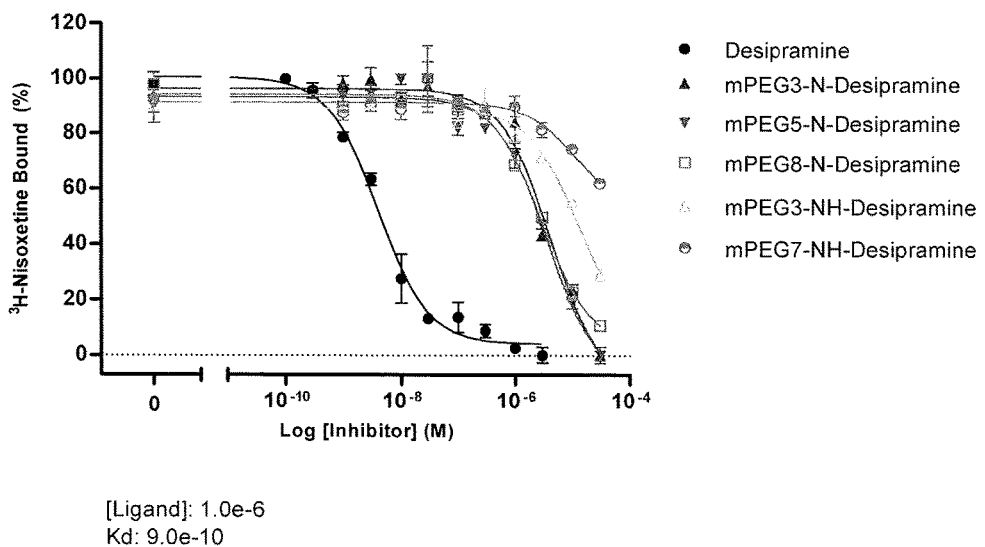
FIG. 4 shows mean (±SEM) percent specific binding of desipramine and its conjugates to noradrenalin transporters in rat forebrain membranes.

$IC_{50}$ values were obtained from non-linear regression analysis of dose-response curves (FIG. 4) and were calculated for those compounds that showed >50% inhibition of binding at the highest concentration tested. $K_i$ was obtained using the Cheng Prusoff correction using experimental $K_d$ values that were previously determined under these assay conditions.

The binding affinities of desipramine and mPEG-desipramine conjugates are shown in Table 4. PEG-desipramine conjugates displayed lower affinity to noradrenalin transporters relative to desipramine. PEG conjugation resulted in greater than 739-folds reduction in binding affinity, and this effect was dependent on chemistry at the conjugation site.

Compared to the parent, the loss in binding affinity was smaller for mPEG-N— than those for mPEG-NH— conjugates at similar PEG sizes (739 to 1058-folds and 2972 to 3336-folds, respectively, relative to parent).

TABLE 4

Summary of binding affinity to noradrenalin transporters.

| Test Compound | MW (Da) | Ki (μM) | Fold Change Relative to Parent |
|---|---|---|---|
| Desipramine | 302.9 | 0.002 | 1 |
| mPEG3-N-Desipramine | 412.6 | 2.11 | 1058 |
| mPEG5-N-Desipramine | 500.7 | 1.83 | 920 |
| mPEG8-N-Desipramine | 632.8 | 1.47 | 739 |
| mPEG3-NH-Desipramine | 398.26 | 6.65 | 3336 |
| mPEG7-NH-Desipramine | 574.36 | 5.92 | 2972 |

Example 8

Muscarinic Receptor Binding Assay

The receptor binding affinities of amitriptyline and four amitriptyline-PEG conjugates were evaluated using radioligand binding assays in membranes prepared from CHO cells that express the recombinant human M1, M2, M3, M4 or M5 muscarinic acetylcholine receptors. Competition binding experiments were conducted by incubating membranes with a fixed concentration of radioligand in the presence of variable concentrations of test compounds. $^3$H—N-Methylscopolamine at 0.8 nM was used as the radioligand for all receptor subtypes. Incubations were carried out for 2 hours at 25° C. in buffer containing 50 mM Tris HCl, 10 mM MgCl$_2$ and 1 mM EDTA. Following incubations, the membranes were washed the bound radioactivity was measured. Non-specific binding was measured in the presence of excess Atropine as the cold ligand and subtraction of this value from the total binding yielded the specific binding at each test compound concentration. $IC_{50}$ values were obtained from non-linear regression analysis of dose-response curves and were calculated only for those compounds that showed >50% inhibition of binding at the highest concentration tested. Ki was obtained using the Cheng Prusoff correction using Kd values that were experimental determined previously under these assay conditions.

The binding affinities of amitriptyline and the PEG conjugates at the five muscarinic receptor subtypes are shown in Table 1. Amitriptyline displayed high binding affinity to all muscarinic receptor subtypes, with Ki values ranging from ~10-90 nM and displayed little selectivity for any muscarinic receptor subtype. In contrast, the PEG conjugates displayed a marked reduction in binding affinity at all subtypes—the Ki at any particular receptor subtype was reduced 10-100-fold. In several cases, a significant inhibition of radioligand binding could not be obtained at the highest concentration tested and hence data are shown as "no significant binding". These data suggest that PEG conjugation significantly reduces the binding affinity of amitriptyline to muscarinic acetylcholine receptors.

| Molecule | Ki (nM) | | | | |
|---|---|---|---|---|---|
| | M1 | M2 | M3 | M4 | M5 |
| Amitriptyline | 9.83 | 87.1 | 35.4 | 23.9 | 17 |
| mPEG-3-Amitriptyline | No significant binding | No significant binding | No significant binding | No significant binding | No significant binding |
| mPEG-5-Amitriptyline | No significant binding | No significant binding | No significant binding | No significant binding | No significant binding |
| mPEG-6-Amitriptyline | 869 | 1170 | No significant binding | No significant binding | No significant binding |
| mPEG-7-Amitriptyline | No significant binding | 1140 | No significant binding | No significant binding | No significant binding |

Example 9

Analgesic Assay

An analgesic assay was used to determine whether a given compound can reduce and/or prevent visceral pain in mice.

The assay utilized CD-1 male mice (5-8 mice per group), each mouse being approximately 0.015-0.030 kg on the study day. Mice were treated according to standard protocols.

Mice were given a single "pretreatment" dose of a compound lacking covalent attachment of a water-soluble, non-peptidic oligomer, a corresponding version comprising the compound covalently attached to a water-soluble, non-peptidic oligomer, or control solution (IV, SC, IP or orally) thirty minutes prior to the administration of the acetic acid solution. The animal was given an IP injection of an irritant (acetic acid) that induces "writhing" which may include: contractions of the abdomen, twisting and turning of the trunk, arching of the back and the extension of the hindlimbs. Mice were given a single IP injection (0.1 mL/10 g bodyweight) of a 0.5% acetic acid solution. After the injection the animals were returned to their observation enclosure and their behavior was observed. Contractions were counted between 0 and 20 minutes after the injection. The animals were used once. Each tested article was dosed at 1, 3 and 10 mg/kg (n=5 animals/dose).

Figure 5:
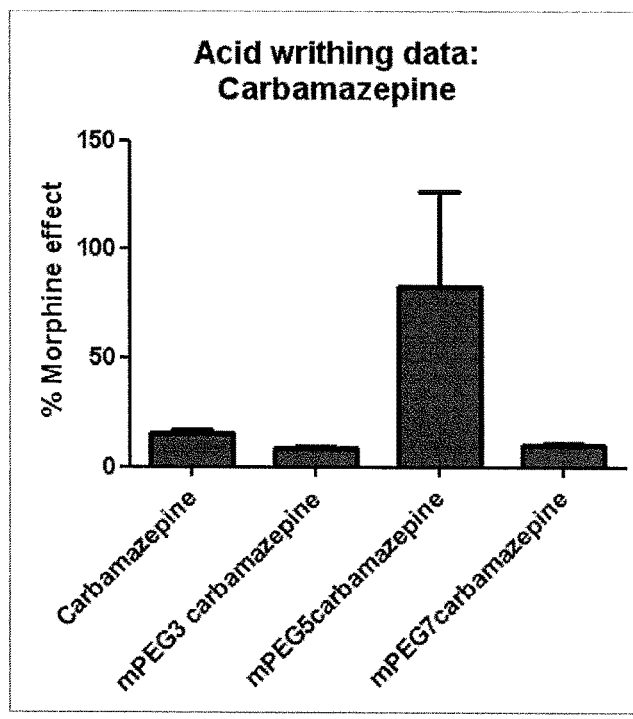
FIG. 5 shows the analgesia activity of the tested compound against the standard analgesic, morphine.

FIG. 5 shows the analgesia activity of the tested compound against the standard analgesic, morphine.

What is claimed is:

1. A method of treatment, comprising administering a stable conjugate selected from:

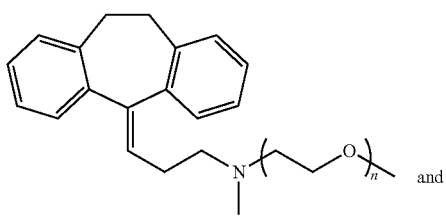 and

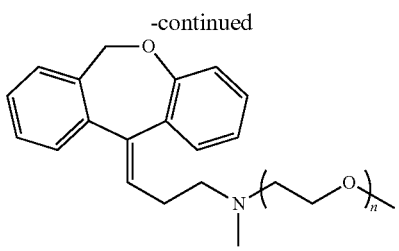

wherein n is an integer from 1 to 30, to a patient in need thereof;

wherein the compound is administered for sedative, hypnotic, anti-anxiety, tranquilizing, anti convulsant, muscle relaxant, anti-depressant, or analgesic effect.

2. The method of claim 1, wherein n is an integer from 1 to 10.

3. The method of claim 2, wherein the stable conjugate has the structure:

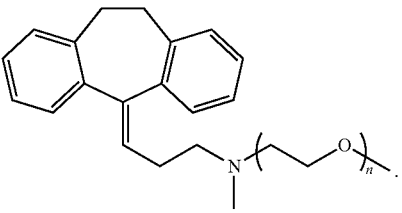

4. The method of claim 3, wherein n is 3, 5, 6, or 7.

5. The method of claim 2, wherein the stable conjugate has the structure:

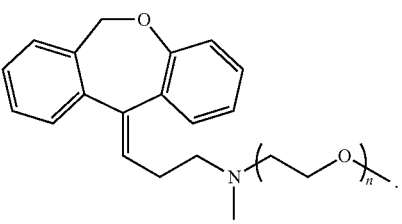

6. The method of claim 1, wherein the stable conjugate is administered to treat pain.

7. The method of claim 6, wherein the stable conjugate is administered to treat neuropathic pain.

8. The method of claim 6, wherein the stable conjugate is administered to treat visceral pain.

9. A method of claim 1, wherein the stable conjugate is administered as a pharmaceutical composition comprising the stable conjugate, and optionally, a pharmaceutically acceptable excipient.

10. The method of claim 9, wherein the pharmaceutical composition is suitable for oral administration.

11. The method of claim 1, wherein the stable conjugate is administered as a unit dosage form.

* * * * *